United States Patent
Wilting et al.

(10) Patent No.: US 6,630,340 B2
(45) Date of Patent: Oct. 7, 2003

(54) FAMILY 5 XYLOGLUCANASES

(75) Inventors: Reinhard Wilting, Farum (DK); Mads Eskelund Bjørnvad, Frederiksberg (DK); Markus Sakari Kauppinen, Smørum (DK); Martin Schulein, deceased, late of Copenhagen (DK), by Hanne Dela, legal representative

(73) Assignee: Novozymes A/S, Bagvaerd (DK)

( * ) Notice: Subject to any disclaimer, the term of this patent is extended or adjusted under 35 U.S.C. 154(b) by 0 days.

(21) Appl. No.: 09/797,464

(22) Filed: Mar. 1, 2001

(65) Prior Publication Data

US 2003/0022807 A1 Jan. 30, 2003

Related U.S. Application Data

(60) Provisional application No. 60/191,620, filed on Mar. 23, 2000.

(30) Foreign Application Priority Data

Mar. 1, 2000 (DK) ......................................... 2000 00326

(51) Int. Cl.$^7$ ............................ C12P 21/06; C12N 1/20; C12N 9/00; C12N 9/14; C12N 9/24; C12N 9/42; C12N 15/00; C07H 21/04

(52) U.S. Cl. ....................... 435/209; 435/69.1; 435/183; 435/195; 435/200; 435/262; 435/263; 435/264; 536/23.2; 536/23.7; 510/114

(58) Field of Search .................. 435/69.1, 183, 435/195, 200, 209, 262, 263, 264; 536/23.2, 23.7; 510/114

(56) References Cited

FOREIGN PATENT DOCUMENTS

| WO | 94/14953 | 7/1994 |
|---|---|---|
| WO | 99/02663 | 1/1999 |

OTHER PUBLICATIONS

Blanco et al. GenBank Accession No. O08342, Jul. 1, 1997.*
Baird et al. GenBank Accession No. P23548, Jul. 15, 1998.*
Blanco et al., Appl Microbiol Biotechnol (1998) 50: 48–54.
Vincken et al., Carbohydrate Research 298 (1997) 299–310.
Ohsumi et al., Plant Cell Physiol. 35(6):963–967 (1994).
McDougall et al., J. Plant Physiol. vol. 143 pp. 591–595 (1994).
Acebes et al., Phytochemistry, vol. 33, No. 6, pp. 1343–1345, (1993).

* cited by examiner

*Primary Examiner*—Rebecca E. Prouty
*Assistant Examiner*—Manjunath N. Rao
(74) *Attorney, Agent, or Firm*—Elias J. Lambris

(57) ABSTRACT

The present invention relates to xyloglucanases belonging to family 5 of glycosyl hydrolases are derived from strains of Paenibacillus, especially from strains of *Paenibacillus pabuli*. The xyloglucanases show high performance in conventional liquid detergent compositions.

20 Claims, No Drawings

FAMILY 5 XYLOGLUCANASES

CROSS-REFERENCE TO RELATED APPLICATIONS

This application claims priority under 35 U.S.C. 119 of Danish application PA 2000 00326 filed Mar. 1, 2000, and U.S. provisional application No. 60/191,620, filed Mar. 23, 2000, the contents of which are fully incorporated herein by reference.

BACKGROUND OF THE INVENTION

1. Field of the Invention

The present invention relates to xyloglucanases belonging to family 5 of glycosyl hydrolases, preferably to enzymes exhibiting xyloglucanase activity as their major enzymatic activity in the neutral and alkaline pH ranges; to a method of producing such enzymes; and to methods for using such enzymes in the textile, detergent and cellulose fiber processing industries.

2. Description of Related Art

Xyloglucan is a major structural polysaccharide in the primary (growing) cell wall of plants. Structurally, xyloglucans consists of a cellulose-like beta-1,4-linked glucose backbone, which is frequently substituted with various side chains. The xyloglucans of most dicotyledonous plants, some monocotyledons and gymnosperms are highly branched polysaccharides in which approx. 75% of the glucose residues in the backbone bear a glycosyl side chain at O-6. The glycosyl residue that is directly attached to the branched glucose residue is invariably alfa-D-xylose. Up to 50% of the side chains in the xyloglucans contain more than one residue due to the presence of beta-D-galactose or alfa-L-fucose-(1-2)-beta-D-galactose moieties at O-2 of the xylose residues (C. Ohsumi and T. Hayashi (1994) Plant and Cell Physiology 35:963–967; G. J. McDougall and S. C. Fry (1994) Journal of Plant Physiology 143:591–595; J. L. Acebes et al. (1993) Phytochemistry 33:1343–1345). On acid hydrolysis, the xyloglucan extracted from cotton fibers yielded glucose, xylose, galactose and fucose in the ratio of 50:29:12:7 (Hayashi et al., 1988).

Xyloglucans produced by solanaceous plants are unusual in that typical only 40% of the beta-1,4-linked glucose residues bear a glycosyl side chain at O-6. Furthermore, up to 60% of the xylose residues are substituted at O-2 with alfa-L-arabinose residues and some solanaceous plants, such as potato, also have xyloglucans with beta-D-galactose substituents at O-2 of some of the xylose residues (York et al (1996)).

Xyloglucan is believed to function in the primary wall of plants by cross-linking cellulose-micro fibrils, forming a cellulose-xyloglucan network. This network is considered necessary for the structural integrity of primary cell-walls (Carpita et al., 1993). Another important function of xyloglucan is to act as a repository for xyloglucan subunit oligosaccharides that are physiologically active regulators of plant cell growth. Xyloglucan subunits may also modulate the action of a xyloglucan endotransglycosylase (XET), a cell wall associated enzyme that has been hypothesized to play a role in the elongation of plant cell walls. Therefore xyloglucan might play an important role in wall loosening and consequently cell expansion (Fry et al., 1992).

The seeds of many dicotyledonous species contain xyloglucan as the major polysaccharide storage reserve. This type of xyloglucan, which is localized in massive thickenings on the inside of the seed cotyledon cell wall, is composed mainly of glucose, xylose and galactose (Rose et al., 1996).

Seeds of the tamarind tree *Tamarindus indica* became a commercial source of gum in 1943 when the gum was found useful as a paper and textile size. Sizing of jute and cotton with tamarind xyloglucan has been extensively practiced in Asia owing to the low cost of the gum and to its excellent properties. Food applications of tamarind xyloglucan include use in confections, jams and jellies and as a stabilizer in ice cream and mayonnaise (Whistler et al., 1993).

Xyloglucanase activity is not included in the classification of enzymes provided by the Enzyme Nomenclature (1992). Hitherto, this enzymatic activity has simply been classified as glucanase activity and has often been believed to be identical to cellulolytic activity (EC 3.2.1.4), i.e. activity against β-1,4-glycosidic linkages in cellulose or cellulose derivative substrates, or at least to be a side activity in enzymes having cellulolytic activity. However, a true xyloglucanase is a true xyloglucan specific enzyme capable of catalyzing the solubilisation of xyloglucan to xyloglucan oligosaccharides but which does not exhibit substantial cellulolytic activity, e.g. activity against the conventionally used cellulose-like substrates CMC (carboxymethylcellulose), HE cellulose and Avicel (microcrystalline cellulose). A xyloglucanase cleaves the beta-1,4-glycosidic linkages in the backbone of xyloglucan.

Xyloglucanase activity is described by Vincken et al. (1997) who characterizes three different endoglucanases from *Trichoderma viride* (similar to *T. reesei*) which all have high activity against cellulose or CMC and show that the EndoI (belonging to family 5 of glycosyl hydrolases, see Henrissat, B. et al. (1991, 1993)) has essentially no (i.e. very little) activity against xyloglucan, and that EndoV (belonging to the family 7 of glycosyl hydrolases) and EndoIV (belonging to the family 12 of glycosyl hydrolases) both have activity against xyloglucan and CMC, respectively, of the same order of magnitude.

International Patent Publication WO 94/14953 discloses a family 12 xyloglucanase (EG II) cloned from the fungus *Aspergillus aculeatus* and expressed in the fungus *Aspergillus oryzae*.

International Patent Publication WO 99/02663 discloses xyloglucanases cloned from *Bacillus licheniformis* (family 12) and *Bacillus agaradhaerens* (family 5) and expressed in *Bacillus subtilis*.

It is an object of the present invention to provide an enzyme with a high xyloglucanase activity, which have an excellent performance in conventional detergent compositions, especially liquid detergents for household laundering.

SUMMARY OF THE INVENTION

The inventors have now found enzymes having substantial xyloglucanase activity, which enzymes belong to family 5 of glycosyl hydrolases and exhibit excellent performance in conventional detergent compositions, especially liquid detergent compositions. All the found xyloglucanases are endogenous to a strain belonging to *Paenibacillus pabuli* or *Paenibacillus sp*.

Accordingly, the present invention relates to a xyloglucanase enzyme belonging to family 5 of glycosyl hydrolases, which enzyme is endogenous to a strain of Paenibacillus. Preferably, the strain of Paenibacillus belongs to the group consisting of the species *Paenibacillus pabuli*, the strain Paenibacillus sp., DSM 13330, and strains of Paenibacillus sp. having a higher degree of identity with the *Paenibacillus pabuli* type strain ATCC 43899 than the strain Paenibacillus sp., DSM 13330, when subjected to 16S RNA analysis.

The inventors have also succeeded in cloning and expressing a family 5 xyloglucanase from the above species and strains, i.e. the invention relates in further aspects to a family 5 xyloglucanase which is (a) a polypeptide encoded by the DNA sequence of positions 840–1931 of SEQ ID NO: 1, (b) a polypeptide produced by culturing a cell comprising the sequence of SEQ ID NO: 1 under conditions wherein the DNA sequence is expressed; (c) a xyloglucanase enzyme having a sequence of at least 85% identity to positions 33–395 of SEQ ID NO: 2 when identity is determined by GAP provided in the GCG program package using a GAP creation penalty of 3.0 and GAP extension penalty of 0.1; or (d) a polypeptide encoded by the xyloglucanase encoding part of the DNA sequence obtainable from the plasmid in *Escherichia coli* DSM 13183; and to an isolated polynucleotide molecule encoding a polypeptide having xyloglucanase activity which polynucleotide molecule hybridizes to a denatured double-stranded DNA probe under medium stringency conditions, wherein the probe is selected from the group consisting of DNA probes comprising the sequence shown in positions 840–1931 of SEQ ID NO: 1, positions 693–1896 of SEQ ID NO:3, and DNA probes comprising a subsequence of positions 840–1931 of SEQ ID NO:1 or positions 693–1896 of SEQ ID NO:3, the subsequence having a length of at least about 100 base pairs.

In further aspects, the invention provides an expression vector comprising a DNA segment which is e.g. a polynucleotide molecule of the invention; a cell comprising the DNA segment or the expression vector; and a method of producing a exhibiting xyloglucanase enzyme, which method comprises culturing the cell under conditions permitting the production of the enzyme, and recovering the enzyme from the culture.

In yet another aspect the invention provides an isolated family 5 xyloglucanase enzyme characterized in (i) being free from homologous impurities and (ii) being produced by the method described above.

The novel enzyme of the present invention is useful for the treatment of cellulosic material, especially cellulose-containing fiber, yarn, woven or non-woven fabric. The treatment can be carried out during the processing of cellulosic material into a material ready for garment manufacture or fabric manufacture, e.g. in the desizing or scouring step; or during industrial or household laundering of such fabric or garment.

Accordingly, in further aspects the present invention relates to a detergent composition comprising a xyloglucanase enzyme having substantial xyloglucanase activity in the neutral or alkaline range; and to use of the enzyme of the invention for the treatment of cellulose-containing fibers, yarn, woven or non-woven fabric.

The present invention has now made it possible to use a xyloglucanase in detergent compositions for removing or bleaching certain soils or stains present on laundry, especially soils and spots resulting from xyloglucan-containing food, plants, and the like. Further, it is contemplated that treatment with detergent compositions comprising the novel enzyme can prevent binding of certain soils to the xyloglucan left on the cellulosic material.

DETAILED DESCRIPTION OF THE INVENTION

Microbial Sources

For the purpose of the present invention the term "obtained from" or "obtainable from" as used herein in connection with a specific source, means that the enzyme is produced or can be produced by the specific source, or by a cell in which a gene from the source have been inserted.

It is at present contemplated that the xyloglucanase of the invention may be obtained from a gram-positive bacterium belonging to a strain of the genus Bacillus, in particular a strain of Paenibacillus.

In a preferred embodiment, the xyloglucanase of the invention is obtained from the species *Paenibacillus pabuli* that is represented by the type strain ATCC 43899, this type strain being publicly available from American Type Culture Collection (ATCC). It is at present contemplated that a DNA sequence encoding an enzyme with an amino acid sequence identity of at least 85% to the enzyme of the invention may be obtained from other strains belonging to the species *Paenibacillus pabuli* and such strains belonging to the species Paenibacillus sp. which, when subjected to a conventional 16S RNA analysis, have a higher degree of identity with the *Paenibacillus pabuli* type strain ATCC 43899 than the strain Paenibacillus sp., DSM 13330. It is contemplated that the strain Paenibacillus sp., DSM 13330, has an identity, compared with the strain *Paenibacillus pabuli* ATCC 43899, of at least 95%, more specifically of at least 97%.

Further, the strain Paenibacillus sp. was deposited by the inventors according to the Budapest Treaty on the International Recognition of the Deposit of Microorganisms for the Purposes of Patent Procedure at the Deutsche Sammlung von Mikroorganismen und Zellkulturen GmbH, Mascheroder Weg 1b, D-38124 Braunschweig, Federal Republic of Germany, on Feb. 18, 2000 under the deposition number DSM 13330. The deposit was made by Novo Nordisk A/S and was later assigned to Novozymes A/S.

A plasmid comprising a DNA sequence encoding a xyloglucanase of the invention has been transformed into a strain of the *Escherichia coli* which was deposited by the inventors according to the Budapest Treaty on the International Recognition of the Deposit of Microorganisms for the Purposes of Patent Procedure at the Deutsche Sammlung von Mikroorganismen und Zellkulturen GmbH, Mascheroder Weg 1b, D-38124 Braunschweig, Federal Republic of Germany, on Dec. 6, 1999 under the deposition number DSM 13183. The deposit was made by Novo Nordisk A/S and was later assigned to Novozymes A/S. It is contemplated that the DNA sequence of this plasmid comprises the DNA sequence of SEQ ID NO: 1.

Definitions

In the present context, the term "enzyme preparation" is intended to mean either be a conventional enzymatic fermentation product, possibly isolated and purified, from a single species of a microorganism, such preparation usually comprising a number of different enzymatic activities; or a mixture of monocomponent enzymes, preferably enzymes derived from bacterial or fungal species by using conventional recombinant techniques, which enzymes have been fermented and possibly isolated and purified separately and which may originate from different species, preferably fungal or bacterial species; or the fermentation product of a microorganism which acts as a host cell for expression of a recombinant xyloglucanase, but which microorganism simultaneously produces other enzymes, e.g. xyloglucanases, proteases, or cellulases, being naturally occurring fermentation products of the microorganism, i.e. the enzyme complex conventionally produced by the corresponding naturally occurring microorganism.

In the present context the term "expression vector" denotes a DNA molecule, linear or circular, that comprises a segment encoding a polypeptide of interest operably linked to additional segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both. The expression vector of the invention may be any expression vector that is conveniently subjected to recombinant DNA procedures, and the choice of vector will often depend on the host cell into which the vector is to be introduced. Thus, the vector may be an autonomously replicating vector, i.e. a vector that exists as an extra chromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The term "recombinant expressed" or "recombinantly expressed" used herein in connection with expression of a polypeptide or protein is defined according to the standard definition in the art. Recombinant expression of a protein is generally performed by using an expression vector as described immediately above.

The term "isolated", when applied to a polynucleotide molecule, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774–78, 1985). The term "an isolated polynucleotide" may alternatively be termed "a cloned polynucleotide".

When applied to a protein/polypeptide, the term "isolated" indicates that the protein is found in a condition other than its native environment. In a preferred form, the isolated protein is substantially free of other proteins, particularly other homologous proteins (i.e. "homologous impurities" (see below)). It is preferred to provide the protein in a greater than 40% pure form, more preferably greater than 60% pure form.

Even more preferably it is preferred to provide the protein in a highly purified form, i.e., greater than 80% pure, more preferably greater than 95% pure, and even more preferably greater than 99% pure, as determined by SDS-PAGE.

The term "isolated protein/polypeptide may alternatively be termed "purified protein/polypeptide".

The term "homologous impurities" means any impurity (e.g. another polypeptide than the polypeptide of the invention), which originate from the homologous cell where the polypeptide of the invention is originally obtained.

The term "obtained from" as used herein in connection with a specific microbial source, means that the polynucleotide and/or polypeptide produced by the specific source, or by a cell in which a gene from the source have been inserted.

The term "operably linked", when referring to DNA segments, denotes that the segments are arranged so that they function in concert for their intended purposes, e.g. transcription initiates in the promoter and proceeds through the coding segment to the terminator.

The term "polynucleotide" denotes a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules.

The term "complements of polynucleotide molecules" denotes polynucleotide molecules having a complementary base sequence and reverse orientation as compared to a reference sequence. For example, the sequence 5' ATG-CACGGG 3' is complementary to 5' CCCGTGCAT 3'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "promoter" denotes a portion of a gene containing DNA sequences that provide for the binding of RNA polymerase and initiation of transcription. Promoter sequences are commonly, but not always, found in the 5' non-coding regions of genes.

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger peptide is commonly cleaved to remove the secretory peptide during transit through the secretory pathway.

Polynucleotides

Within preferred embodiments of the invention an isolated polynucleotide of the invention will hybridize to similar sized regions of SEQ ID NO: 1 or SEQ ID NO: 3, or a sequence complementary thereto, under at least medium stringency conditions.

In particular polynucleotides of the invention will hybridize to a denatured double-stranded DNA probe comprising either the full sequence shown in SEQ ID NO: 1 or the sequence shown in positions 840–1931 of SEQ ID NO: 1 or the full sequence shown in SEQ ID NO: 3 or the sequence shown in positions 693–1896 of SEQ ID NO: 3 or any probe comprising a subsequence of SEQ ID NO: 5 or SEQ ID NO: 3 having a length of at least about 100 base pairs under at least medium stringency conditions, but preferably at high stringency conditions as described in detail below. Suitable experimental conditions for determining hybridization at medium or high stringency between a nucleotide probe and a homologous DNA or RNA sequence involve pre-soaking of the filter containing the DNA fragments or RNA to hybridize in 5×SSC (Sodium chloride/Sodium citrate, Sambrook et al. 1989) for 10 min, and prehybridization of the filter in a solution of 5×SSC, 5×Denhardt's solution (Sambrook et al. 1989), 0.5% SDS and 100 $\mu$g/ml of denatured sonicated salmon sperm DNA (Sambrook et al. 1989), followed by hybridization in the same solution containing a concentration of 10 ng/ml of a random-primed (Feinberg, A. P. and Vogelstein, B. (1983) Anal. Biochem. 132:6–13), 32P-dCTP-labeled (specific activity higher than 1×10⁹ cpm/$\mu$g) probe for 12 hours at ca. 45° C. The filter is then washed twice for 30 minutes in 2×SSC, 0.5% SDS at least 60° C. (medium stringency), still more preferably at least 65° C. (medium/high stringency), even more preferably at least 70° C. (high stringency), and even more preferably at least 75° C. (very high stringency).

Molecules to which the oligonucleotide probe hybridizes under these conditions are detected using an x-ray film.

As previously noted, the isolated polynucleotides of the present invention include DNA and RNA. Methods for isolating DNA and RNA are well known in the art. DNA and RNA encoding genes of interest can be cloned in Gene Banks or DNA libraries by means of methods known in the art.

Polynucleotides encoding polypeptides having endoglucanase activity of the invention are then identified and isolated by, for example, hybridization or PCR.

The present invention further provides counterpart polypeptides and polynucleotides from different bacterial strains (orthologs or paralogs). Of particular interest are xyloglucanase polypeptides from gram-positive alkalophilic strains, including species of Bacillus. Of special interest are xyloglucanase peptides from strains of Paenibacillus, which are very closely related to the species *Paenibacillus pabuli*, exemplified by the strain ATCC 43899 that is the type strain of *Paenibacillus pabuli*.

Species homologues of a polypeptide with xyloglucanase activity of the invention can be cloned using information and compositions provided by the present invention in combination with conventional cloning techniques. For example, a DNA sequence of the present invention can be cloned using chromosomal DNA obtained from a cell type that expresses the protein. Suitable sources of DNA can be identified by probing Northern blots with probes designed from the sequences disclosed herein. A library is then prepared from chromosomal DNA of a positive cell line. A DNA sequence of the invention encoding an polypeptide having xyloglucanase activity can then be isolated by a variety of methods, such as by probing with probes designed from the sequences disclosed in the present specification and claims or with one or more sets of degenerate probes based on the disclosed sequences. A DNA sequence of the invention can also be cloned using the polymerase chain reaction, or PCR (Mullis, U.S. Pat. No. 4,683,202), using primers designed from the sequences disclosed herein. Within an additional method, the DNA library can be used to transform or transfect host cells, and expression of the DNA of interest can be detected with an antibody (monoclonal or polyclonal) raised against the xyloglucanase cloned from *Paenibacillus pabuli*, e.g. from the type strain deposited as ATCC 43899, or from *Paenibacillus sp.*, DSM 13330, expressed and purified as described in Materials and Methods and the examples, or by an activity test relating to a polypeptide having xyloglucanase activity.

Polypeptides

The sequence of amino acids in positions 33–395 of SEQ ID NO: 2 and positions 33–400 of SEQ ID NO: 4, respectively, is a mature xyloglucanase sequence comprising the catalytic active domain.

The sequence of amino acids of SEQ ID NOS: 5–9 represents N-terminal or C-terminal sequences of mature xyloglucanase sequences, cf. example 2.

The present invention also provides xyloglucanase polypeptides that are substantially homologous to the polypeptide of amino acids in position 33–395 of SEQ ID NO: 2 and species homologs (paralogs or orthologs) thereof. The term "substantially homologous" is used herein to denote polypeptides having 85%, preferably at least 88%, more preferably at least 90%, and even more preferably at least 95%, sequence identity to the sequence shown in amino acids nos. 33–395 of SEQ ID NO: 2 or its orthologs or paralogs. Such polypeptides will more preferably be at least 98% identical to the sequence shown in amino acids in positions 33–395 of SEQ ID NO: 2 or its orthologs or paralogs. Percent sequence identity is determined by conventional methods, by means of computer programs known in the art such as GAP provided in the GCG program package (Program Manual for the Wisconsin Package, Version 8, August 1994, Genetics Computer Group, 575 Science Drive, Madison, Wis., USA 53711) as disclosed in Needleman, S. B. and Wunsch, C. D., (1970), Journal of Molecular Biology, 48, 443–453, which is hereby incorporated by reference in its entirety. GAP is used with the following settings for polypeptide sequence comparison: GAP creation penalty of 3.0 and GAP extension penalty of 0.1. The following sequence identity was found for the appended SEQ ID NOS: 2 and 4:

|          | SEQ ID #2 | SEQ ID #4 |
|----------|-----------|-----------|
| SEQ ID #2 | 100%      | 88%       |

Sequence identity of polynucleotide molecules is determined by similar methods using GAP with the following settings for DNA sequence comparison: GAP creation penalty of 5.0 and GAP extension penalty of 0.3.

Substantially homologous proteins and polypeptides are characterized as having one or more amino acid substitutions, deletions or additions. These changes are preferably of a minor nature, that is conservative amino acid substitutions (see Table 2) and other substitutions that do not significantly affect the folding or activity of the protein or polypeptide; small deletions, typically of one to about 30 amino acids; and small amino- or carboxyl-terminal extensions, such as an amino-terminal methionine residue, a small linker peptide of up to about 20–25 residues, or a small extension that facilitates purification (an affinity tag), such as a poly-histidine tract, protein A (Nilsson et al., *EMBO J.* 4:1075, 1985; Nilsson et al., *Methods Enzymol.* 198:3, 1991. See, in general Ford et al., *Protein Expression and Purification* 2: 95–107, 1991, which is incorporated herein by reference. DNAs encoding affinity tags are available from commercial suppliers (e.g., Pharmacia Biotech, Piscataway, N.J.; New England Biolabs, Beverly, Mass.).

However, even though the changes described above preferably are of a minor nature, such changes may also be of a larger nature such as fusion of larger polypeptides of up to 300 amino acids or more both as amino- or carboxyl-terminal extensions to a polypeptide of the invention having xyloglucanase activity.

TABLE 1

| Conservative amino acid substitutions | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

In addition to the 20 standard amino acids, non-standard amino acids (such as 4-hydroxyproline, 6-N-methyl lysine, 2-aminoisobutyric acid, isovaline and a-methyl serine) may be substituted for amino acid residues of a polypeptide according to the invention. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, or preferably, are commercially available, and include pipecolic acid, thiazolidine carboxylic acid, dehydroproline, 3- and 4-methylproline, and 3,3-dimethylproline.

Essential amino acids in the xyloglucanase polypeptides of the present invention can be identified according to procedures known in the art, such as site-directed mutagenesis or alanine-scanning mutagenesis (Cunningham and Wells, *Science* 244: 1081–1085, 1989). In the latter technique, single alanine mutations are introduced at every residue in the molecule, and the resultant mutant molecules are tested for biological activity (i.e. xyloglucanase activity) to identify amino acid residues that are critical to the activity of the molecule. See also, Hilton et al., *J. Biol. Chem.* 271:4699–4708, 1996. The active site of the enzyme or other biological interaction can also be determined by physical analysis of structure, as determined by such techniques as nuclear magnetic resonance, crystallography, electron diffraction or photo affinity labeling, in conjunction with mutation of putative contact site amino acids. See, for example, de Vos et al., *Science* 255:306–312, 1992; Smith et al., *J. Mol. Biol.* 224:899–904, 1992; Wlodaver et al., *FEBS Lett.* 309:59–64, 1992. The identities of essential amino acids can also be inferred from analysis of homologies with polypeptides, which are related to a polypeptide according to the invention.

Multiple amino acid substitutions can be made and tested using known methods of mutagenesis, recombination and/or shuffling followed by a relevant screening procedure, such as those disclosed by Reidhaar-Olson and Sauer (*Science* 241:53–57, 1988), Bowie and Sauer (*Proc. Natl. Acad. Sci. USA* 86:2152–2156, 1989), WO95/17413, or WO 95/22625. Briefly, these authors disclose methods for simultaneously randomizing two or more positions in a polypeptide, or recombination/shuffling of different mutations (WO95/17413, WO95/22625), followed by selecting for functional a polypeptide, and then sequencing the mutagenized polypeptides to determine the spectrum of allowable substitutions at each position. Other methods that can be used include phage display (e.g., Lowman et al., *Biochem.* 30:10832–10837, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Mutagenesis/shuffling methods as disclosed above can be combined with high-throughput, automated screening methods to detect activity of cloned, mutagenized polypeptides in host cells. Mutagenized DNA molecules that encode active polypeptides can be recovered from the host cells and rapidly sequenced using modern equipment. These methods allow the rapid determination of the importance of individual amino acid residues in a polypeptide of interest, and can be applied to polypeptides of unknown structure.

Using the methods discussed above, one of ordinary skill in the art can identify and/or prepare a variety of polypeptides that are substantially homologous or identical to residues 33 to 395 of SEQ ID NO: 2 and retain the xyloglucanase activity of the wild-type protein.

The xyloglucanase enzyme of the invention may, in addition to the enzyme core comprising the catalytically active domain, also comprise a cellulose binding domain (CBD), the cellulose binding domain and enzyme core (the catalytically active domain) of the enzyme being operably linked. The cellulose binding domain (CBD) may exist as an integral part the encoded enzyme, or a CBD from another origin may be introduced into the xyloglucanase thus creating an enzyme hybrid. In this context, the term "cellulose-binding domain" is intended to be understood as defined by Peter Tomme et al. "Cellulose-Binding Domains: Classification and Properties" in "Enzymatic Degradation of Insoluble Carbohydrates", John N. Saddler and Michael H. Penner (Eds.), ACS Symposium Series, No. 618, 1996. This definition classifies more than 120 cellulose-binding domains into 10 families (I-X), and demonstrates that CBDs are found in various enzymes such as cellulases, xylanases, mannanases, arabinofuranosidases, acetyl esterases and chitinases. CBDs have also been found in algae, e.g. the red alga *Porphyra purpurea* as a non-hydrolytic polysaccharide-binding protein, see Tomme et al., op.cit. However, most of the CBDs are from cellulases and xylanases, CBDs are found at the N and C termini of proteins or are internal. Enzyme hybrids are known in the art, see e.g. WO 90/00609 and WO 95/16782, and may be prepared by transforming into a host cell a DNA construct comprising at least a fragment of DNA encoding the cellulose-binding domain ligated, with or without a linker, to a DNA sequence encoding the xyloglucanase and growing the host cell to express the fused gene. Enzyme hybrids may be described by the following formula:

CBD—MR—X wherein CBD is the N-terminal or the C-terminal region of an amino acid sequence corresponding to at least the cellulose-binding domain; MR is the middle region (the linker), and may be a bond, or a short linking group preferably of from about 2 to about 100 carbon atoms, more preferably of from 2 to 40 carbon atoms; or is preferably from about 2 to about 100 amino acids, more preferably of from 2 to 40 amino acids; and X is an N-terminal or C-terminal region of a polypeptide encoded by the polynucleotide molecule of the invention.

Immunological Cross-Reactivity

Polyclonal antibodies, especially monospecific polyclonal antibodies, to be used in determining immunological cross-reactivity may be prepared by use of a purified xyloglucanolytic enzyme. More specifically, antiserum against the xyloglucanase of the invention may be raised by immunizing rabbits (or other rodents) according to the procedure described by N. Axelsen et al. in: A Manual of Quantitative Immunoelectrophoresis, Blackwell Scientific Publications, 1973, Chapter 23, or A. Johnstone and R. Thorpe, Immunochemistry in Practice, Blackwell Scientific Publications, 1982 (more specifically p. 27–31). Purified immunoglobulins may be obtained from the antisera, for example by salt precipitation (($NH_4$)$_2$ $SO_4$), followed by dialysis and ion exchange chromatography, e.g. on DEAE-Sephadex. Immunochemical characterization of proteins may be done either by Outcherlony double-diffusion analysis (O. Ouchterlony in: Handbook of Experimental Immunology (D. M. Weir, Ed.), Blackwell Scientific Publications, 1967, pp. 655–706), by crossed immunoelectrophoresis (N. Axelsen et al., supra, Chapters 3 and 4), or by rocket immunoelectrophoresis (N. Axelsen et al., Chapter 2).

Recombinant Expression Vectors

A recombinant vector comprising a DNA construct encoding the enzyme of the invention may be any vector, which may conveniently be subjected to recombinant DNA procedures, and the choice of vector will often depend on the host cell into which it is to be introduced. Thus, the vector may be an autonomously replicating vector, i.e. a vector that exists as an extra chromosomal entity, the replication of which is independent of chromosomal replication, e.g. a plasmid. Alternatively, the vector may be one which, when introduced into a host cell, is integrated into the host cell genome in part or in its entirety and replicated together with the chromosome(s) into which it has been integrated.

The vector is preferably an expression vector in which the DNA sequence encoding the enzyme of the invention is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the enzyme.

The promoter may be any DNA sequence, which shows transcriptional activity in the host cell of choice and may be derived from genes encoding proteins either homologous or heterologous to the host cell.

Examples of suitable promoters for use in bacterial host cells include the promoter of the *Bacillus stearothermophilus* maltogenic amylase gene, the *Bacillus licheniformis* alpha-amylase gene, the *Bacillus amyloliquefaciens* alpha-amylase gene, the *Bacillus subtilis* alkaline protease gene, or the *Bacillus pumilus* xylosidase gene, or the phage Lambda PR or PL promoters or the *E. coli* lac, trp or tac promoters.

The DNA sequence encoding the enzyme of the invention may also, if necessary, be operably connected to a suitable terminator.

The recombinant vector of the invention may further comprise a DNA sequence enabling the vector to replicate in the host cell in question.

The vector may also comprise a selectable marker, e.g. a gene the product of which complements a defect in the host cell, or a gene encoding resistance to e.g. antibiotics like kanamycin, chloramphenicol, erythromycin, tetracycline, spectinomycine, or the like, or resistance to heavy metals or herbicides.

To direct an enzyme of the present invention into the secretory pathway of the host cells, a secretory signal sequence (also known as a leader sequence, prepro sequence or pre sequence) may be provided in the recombinant vector. The secretory signal sequence is joined to the DNA sequence encoding the enzyme in the correct reading frame. Secretory signal sequences are commonly positioned 5' to the DNA sequence encoding the enzyme. The secretory signal sequence may be that normally associated with the enzyme or may be from a gene encoding another secreted protein.

The procedures used to ligate the DNA sequences coding for the present enzyme, the promoter and optionally the terminator and/or secretory signal sequence, respectively, or to assemble these sequences by suitable PCR amplification schemes, and to insert them into suitable vectors containing the information necessary for replication or integration, are well known to persons skilled in the art (cf., for instance, Sambrook et al., op.cit.).

Host Cells

The cloned DNA molecule introduced into the host cell may be either homologous or heterologous to the host in question. If homologous to the host cell, i.e. produced by the host cell in nature, it will typically be operably connected to another promoter sequence or, if applicable, another secretory signal sequence and/or terminator sequence than in its natural environment. The term "homologous" is intended to include a DNA sequence encoding an enzyme native to the host organism in question. The term "heterologous" is intended to include a DNA sequence not expressed by the host cell in nature. Thus, the DNA sequence may be from another organism, or it may be a synthetic sequence.

The host cell into which the cloned DNA molecule or the recombinant vector of the invention is introduced may be any cell, which is capable of producing the desired enzyme and includes bacteria, yeast, fungi and higher eukaryotic cells.

Examples of bacterial host cells which on cultivation are capable of producing the enzyme of the invention may be a gram-positive bacteria such as a strain of Bacillus, in particular *Bacillus alkalophilus, Bacillus amyloliquefaciens, Bacillus brevis, Bacillus lautus, Bacillus lentus, Bacillus licheniformis, Bacillus circulans, Bacillus coagulans, Bacillus megatherium, Bacillus stearothermophilus, Bacillus subtilis* and *Bacillus thuringiensis*, a strain of Lactobacillus, a strain of Streptococcus, a strain of Streptomyces, in particular *Streptomyces lividans* and *Streptomyces murinus*, or the host cell may be a gram-negative bacteria such as a strain of *Escherichia coli*.

The transformation of the bacteria may be effected by protoplast transformation, electroporation, conjugation, or by using competent cells in a manner known per se (cf. e.g. Sambrook et al., supra).

When expressing the enzyme in bacteria such as *Escherichia coli*, the enzyme may be retained in the cytoplasm, typically as insoluble granules (known as inclusion bodies), or may be directed to the periplasmic space by a bacterial secretion sequence. In the former case, the cells are lysed and the granules are recovered and denatured after which the enzyme is refolded by diluting the denaturing agent. In the latter case, the enzyme may be recovered from the periplasmic space by disrupting the cells, e.g. by sonication or osmotic shock, to release the contents of the periplasmic space and recovering the enzyme.

When expressing the enzyme in gram-positive bacteria such as a strain of Bacillus or a strain of Streptomyces, the enzyme may be retained in the cytoplasm, or may be directed to the extra cellular medium by a bacterial secretion sequence.

Examples of a fungal host cell which on cultivation are capable of producing the enzyme of the invention is e.g. a strain of Aspergillus or Fusarium, in particular *Aspergillus awamori, Aspergillus nidulans, Aspergillus niger, Aspergillus oryzae*, and *Fusarium oxysporum*, and a strain of Trichoderma, preferably *Trichoderma harzianum, Trichoderma reesei* and *Trichoderma viride*.

Fungal cells may be transformed by a process involving protoplast formation and transformation of the protoplasts followed by regeneration of the cell wall in a manner known per se. The use of a strain of Aspergillus as a host cell is described in EP 238 023 (Novo Nordisk A/S), the contents of which are hereby incorporated by reference.

Examples of a host cell of yeast origin which on cultivation are capable of producing the enzyme of the invention is e.g. a strain of Hansenula sp., a strain of Kluyveromyces sp., in particular *Kluyveromyces lactis* and *Kluyveromyces marcianus*, a strain of Pichia sp., a strain of Saccharomyces, in particular *Saccharomyces carlsbergensis, Saccharomyces cerevisae, Saccharomyces kluyveri* and *Saccharomyces uvarum*, a strain of Schizosaccharomyces sp., in particular *Schizosaccharomyces pombe*, and a strain of Yarrowia sp., in particular *Yarrowia lipolytica*.

Examples of a host cell of plant origin which on cultivation are capable of producing the enzyme of the invention is e.g. a plant cell of Solanum tuberosum or Nicotiana tabacum.

Method of Producing a Xyloglucanolytic Enzyme

In another aspect, the present invention also relates to a method of producing the enzyme preparation of the invention, the method comprising culturing a microorganism capable of producing the xyloglucanase under conditions permitting the production of the enzyme, and recovering the enzyme from the culture. Culturing may be carried out using conventional fermentation techniques, e.g. culturing in shake flasks or fermentors with agitation to ensure sufficient aeration on a growth medium inducing production of the xyloglucanase enzyme. The growth medium may contain a conventional N-source such as peptone, yeast extract or casamino acids, a reduced amount of a conventional C-source such as dextrose or sucrose, and an inducer such as xyloglucan or composit plant substrates such as cereal brans (e.g. wheat bran or rice husk). The recovery may be carried out using conventional techniques, e.g. separation of bio-mass and supernatant by centrifugation or filtration, recovery of the supernatant or disruption of cells if the enzyme of interest is intracellular, perhaps followed by further purification as described in EP 0 406 314 or by crystallization as described in WO 97/15660.

Further, the present invention provides a method of producing an isolated enzyme according to the invention, wherein a suitable host cell, which has been transformed with a DNA sequence encoding the enzyme, is cultured under conditions permitting the production of the enzyme, and the resulting enzyme is recovered from the culture.

As defined herein, an isolated polypeptide (e.g. an enzyme) is a polypeptide which is essentially free of other polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE.

The term "isolated polypeptide" may alternatively be termed "purified polypeptide".

When an expression vector comprising a DNA sequence encoding the enzyme is transformed into a heterologous host cell it is possible to enable heterologous recombinant production of the enzyme of the invention.

Thereby it is possible to make a highly purified or monocomponent xyloglucanolytic composition, characterized in being free from homologous impurities.

In this context, homologous impurities mean any impurities (e.g. other polypeptides than the enzyme of the invention), which originate from the homologous cell where the enzyme of the invention is originally obtained.

In the present invention the homologous host cell may be a strain of Paenibacillus sp. or *Paenibacillus pabuli.*

The medium used to culture the transformed host cells may be any conventional medium suitable for growing the host cells in question. The expressed xyloglucanolytic enzyme may conveniently be secreted into the culture medium and may be recovered there from by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

The present invention also relates to a transgenic plant, plant part or plant cell which has been transformed with a DNA sequence encoding the xyloglucanase of the invention so as to express and produce this enzyme in recoverable quantities. The enzyme may be recovered from the plant or plant part.

The transgenic plant can be dicotyledonous or monocotyledonous, for short a dicot or a monocot. Examples of monocot plants are grasses, such as meadow grass (blue grass, Poa), forage grass such as festuca, lolium, temperate grass, such as Agrostis, and cereals, e.g. wheat, oats, rye, barley, rice, sorghum and maize (corn).

Examples of dicot plants are tobacco, legumes, such as lupins, potato, sugar beet, pea, bean and soybean, and cruciferous (family Brassicaceae), such as cauliflower, oil seed rape and the closely related model organism *Arabidopsis thaliana.*

Examples of plant parts are stem, callus, leaves, root, fruits, seeds, and tubers. In the present context, also specific plant tissues, such as chloroplast, apoplast, mitochondria, vacuole, peroxisomes and cytoplasm are considered to be a plant part. Furthermore, any plant cell, whatever the tissue origin, is considered to be a plant part.

Also included within the scope of the invention are the progeny of such plants, plant parts and plant cells.

The transgenic plant or plant cell expressing the enzyme of the invention may be constructed in accordance with methods known in the art. In short the plant or plant cell is constructed by incorporating one or more expression constructs encoding the enzyme of the invention into the plant host genome and propagating the resulting modified plant or plant cell into a transgenic plant or plant cell.

Conveniently, the expression construct is a DNA construct which comprises a gene encoding the enzyme of the invention in operable association with appropriate regulatory sequences required for expression of the gene in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, e.g. based on when, where and how the enzyme is desired to be expressed. For instance, the expression of the gene encoding the enzyme of the invention may be constitutive or inducible, or may be developmental, stage or tissue specific, and the gene product may be targeted to a specific tissue or plant part such as seeds or leaves. Regulatory sequences are e.g. described by Tague et al, Plant, Phys., 86, 506, 1988.

For constitutive expression the 35S-CaMV promoter may be used (Franck et al., 1980. Cell 21: 285–294). Organ-specific promoters may e.g. be a promoter from storage sink tissues such as seeds, potato tubers, and fruits (Edwards & Coruzzi, 1990. Annu. Rev. Genet. 24: 275–303), or from metabolic sink tissues such as meristems (Ito et al., 1994. Plant Mol. Biol. 24: 863–878), a seed specific promoter such as the glutelin, prolamin, globulin or albumin promoter from rice (Wu et al., Plant and Cell Physiology Vol. 39, No. 8 pp. 885–889 (1998)), a *Vicia faba* promoter from the legumin B4 and the unknown seed protein gene from *Vicia faba* described by Conrad U. et al, Journal of Plant Physiology Vol. 152, No. 6 pp. 708–711 (1998), a promoter from a seed oil body protein (Chen et al., Plant and cell physiology vol. 39, No. 9 pp. 935–941 (1998), the storage protein napA promoter from *Brassica napus*, or any other seed specific promoter known in the art, e.g. as described in WO 91/14772. Furthermore, the promoter may be a leaf specific promoter such as the rbcs promoter from rice or tomato (Kyozuka et al., Plant Physiology Vol. 102, No. 3 pp. 991–1000 (1993), the chlorella virus adenine methyltransferase gene promoter (Mitra, A. and Higgins, D. W., Plant Molecular Biology Vol. 26, No. 1 pp. 85–93 (1994), or the aldP gene promoter from rice (Kagaya et al., Molecular and General Genetics Vol. 248, No. 6 pp. 668–674 (1995), or a wound inducible promoter such as the potato pin2 promoter (Xu et al, Plant Molecular Biology Vol. 22, No. 4 pp. 573–588 (1993).

A promoter enhancer element may be used to achieve higher expression of the enzyme in the plant. For instance, the promoter enhancer element may be an intron placed between the promoter and the nucleotide sequence encoding the enzyme. For instance, Xu et al. op cit disclose the use of the first intron of the rice actin 1 gene to enhance expression.

The selectable marker gene and any other parts of the expression construct may be chosen from those available in the art.

The DNA construct is incorporated into the plant genome according to conventional techniques known in the art, including Agrobacterium-mediated transformation, virus-mediated transformation, micro injection, particle bombardment, biolistic transformation, and electroporation (Gasser et al, Science, 244, 1293; Potrykus, Bio/Techn. 8, 535, 1990; Shimamoto et al, Nature, 338, 274, 1989).

Presently, *Agrobacterium tumefaciens* mediated gene transfer is the method of choice for generating transgenic dicots (for review Hooykas & Schilperoort, 1992. Plant Mol. Biol. 19: 15–38), however it can also be used for transforming monocots, although other transformation methods are generally preferred for these plants. Presently, the method of choice for generating transgenic monocots is particle bombardment (microscopic gold or tungsten particles coated with the transforming DNA) of embryonic calli or developing embryos (Christou, 1992. Plant J. 2: 275–281; Shimamoto, 1994. Curr. Opin. Biotechnol. 5: 158–162; Vasil et al., 1992. Bio/Technology 10: 667–674). An alternative method for transformation of monocots is based on protoplast transformation as described by Omirulleh S, et al., Plant Molecular biology Vol. 21, No. 3 pp. 415–428 (1993).

Following transformation, the transformants having incorporated the expression construct are selected and regenerated into whole plants according to methods well known in the art.

The Enzyme

In a preferred embodiment of the present invention, the xyloglucanase has a relative activity at a temperature of 50° C, preferably of at least 60%, preferably at least 70%, compared to the activity at the optimal temperature.

In yet another preferred embodiment, at a temperature of 60° C., the relative xyloglucanase activity is at least 40%, preferably at least 50%; at a temperature of 70° C., the relative xyloglucanase activity is at least 40%, preferably at least 45%, especially at least 50%.

Enzyme Compositions

In a still further aspect, the present invention relates to an enzyme composition comprising an enzyme exhibiting xyloglucanase activity as described above.

The enzyme composition of the invention may, in addition to the xyloglucanase of the invention, comprise one or more other enzyme types, for instance hemicellulase such as xylanase and mannanase, cellulase or endo-β-1,4-glucanase components, chitinase, lipase, esterase, pectinase, cutinase, phytase, oxidoreductase (peroxidase, haloperoxidase, oxidase, laccase), protease, amylase, reductase, phenoloxidase, ligninase, pullulanase, pectate lyase, pectin acetyl esterase, polygalacturonase, rhamnogalacturonase, pectin lyase, pectin methylesterase, cellobiohydrolase, transglutaminase; or mixtures thereof.

The enzyme composition may be prepared in accordance with methods known in the art and may be in the form of a liquid or a dry composition. For instance, the enzyme composition may be in the form of a granulate or a microgranulate. The enzyme to be included in the composition may be stabilized in accordance with methods known in the art.

Xyloglucanases have potential uses in a lot of different industries and applications. Examples are given below of preferred uses of the enzyme composition of the invention. The dosage of the enzyme composition of the invention and other conditions under which the composition is used may be determined based on methods known in the art.

The xyloglucanase or xyloglucanase composition according to the invention may be useful for at least one of the following purposes.

Uses

Use in the Detergent Industry

During washing and wearing, dyestuff from dyed fabrics or garment will conventionally bleed from the fabric, which then looks faded and worn. Removal of surface fibers from the fabric will partly restore the original colours and looks of the fabric. By the term "colour clarification", as used herein, is meant the partly restoration of the initial colours of fabric or garment throughout multiple washing cycles.

The term "de-pilling" denotes removing of pills from the fabric surface.

The term "soaking liquor" denotes an aqueous liquor in which laundry may be immersed prior to being subjected to a conventional washing process. The soaking liquor may contain one or more ingredients conventionally used in a washing or laundering process.

The term "washing liquor" denotes an aqueous liquor in which laundry is subjected to a washing process, i.e. usually a combined chemical and mechanical action either manually or in a washing machine. Conventionally, the washing liquor is an aqueous solution of a powder or liquid detergent composition.

The term "rinsing liquor" denotes an aqueous liquor in which laundry is immersed and treated, conventionally immediately after being subjected to a washing process, in order to rinse the laundry, i.e. essentially remove the detergent solution from the laundry. The rinsing liquor may contain a fabric conditioning or softening composition.

The laundry subjected to the method of the present invention may be conventional washable laundry. Preferably, the major part of the laundry is sewn or unsown fabrics, including knits, wovens, denims, yarns, and towelling, made from cotton, cotton blends or natural or manmade cellulosics (e.g. originating from xylan-containing cellulose fibers such as from wood pulp) or blends thereof. Examples of blends are blends of cotton or rayon/viscose with one or more companion material such as wool, synthetic fibers (e.g. polyamide fibers, acrylic fibers, polyester fibers, polyvinyl alcohol fibers, polyvinyl chloride fibers, polyvinylidene chloride fibers, polyurethane fibers, polyurea fibers, aramid fibers), and cellulose-containing fibers (e.g. rayon/viscose, ramie, flax/linen, jute, cellulose acetate fibers, lyocell).

Detergent Disclosure and Examples

Surfactant System

The detergent compositions according to the present invention comprise a surfactant system, wherein the surfactant can be selected from non-ionic and/or anionic and/or cationic and/or ampholytic and/or zwitterionic and/or semipolar surfactants.

The surfactant is typically present at a level from 0.1% to 60% by weight.

The surfactant is preferably formulated to be compatible with enzyme components present in the composition. In liquid or gel compositions the surfactant is most preferably formulated in such a way that it promotes, or at least does not degrade, the stability of any enzyme in these compositions.

Preferred systems to be used according to the present invention comprise as a surfactant one or more of the non-ionic and/or anionic surfactants described herein.

Polyethylene, polypropylene, and polybutylene oxide condensates of alkyl phenols are suitable for use as the non-ionic surfactant of the surfactant systems of the present invention, with the polyethylene oxide condensates being pre-ferred. These compounds include the condensation products of alkyl phenols having an alkyl group containing from about 6 to about 14 carbon atoms, preferably from about 8 to about 14 carbon atoms, in either a straight chain or branched-chain configuration with the alkylene oxide. In a preferred embodiment, the ethylene oxide is present in an amount equal to from about 2 to about 25 moles, more preferably from about 3 to about 15 moles, of ethylene oxide per mole of alkyl phenol. Commercially available non-ionic surfactants of this type include Igepal™ CO-630, marketed by the GAF Corporation; and Triton™ X-45, X-114, X-100 and X-102, all marketed by the Rohm & Haas Company. These surfactants are commonly referred to as alkyl phenol alkoxylates (e.g., alkyl phenol ethoxylates).

The condensation products of primary and secondary aliphatic alcohols with about 1 to about 25 moles of ethylene oxide are suitable for use as the non-ionic surfactant of the non-ionic surfactant systems of the present invention. The alkyl chain of the aliphatic alcohol can either be straight or branched, primary or secondary, and generally contains from about 8 to about 22 carbon atoms. Preferred are the condensation products of alcohols having an alkyl group containing from about 8 to about 20 carbon atoms, more preferably from about 10 to about 18 carbon atoms, with from about 2 to about 10 moles of ethylene oxide per mole of alcohol. About 2 to about 7 moles of ethylene oxide and most preferably from 2 to 5 moles of ethylene oxide per mole of alcohol are present in said condensation products. Examples of commercially available non-ionic surfactants of this type include Tergitol™ 15-S-9 (The condensation product of $C_{11}$–$C_{15}$ linear alcohol with 9 moles ethylene oxide), Tergitol™ 24-L-6 NMW (the condensation product of $C_{12}$–$C_{14}$ primary alcohol with 6 moles ethylene oxide with a narrow molecular weight distribution), both marketed by Union Carbide Corporation; Neodol™ 45-9 (the condensation product of $C_{14}$–$C_{15}$ linear alcohol with 9 moles of ethylene oxide), Neodol™ 23-3 (the condensation product of $C_{12}$–$C_{13}$ linear alcohol with 3.0 moles of ethylene oxide), Neodol™ 45-7 (the condensation product of $C_{14}$–$C_{15}$ linear alcohol with 7 moles of ethylene oxide), Neodol™ 45-5 (the condensation product of $C_{14}$–$C_{15}$ linear alcohol with 5 moles of ethylene oxide) marketed by Shell Chemical Company, Kyro™ EOB (the condensation product of $C_{13}$–$C_{15}$ alcohol with 9 moles ethylene oxide), marketed by The Procter & Gamble Company, and Genapol LA 050 (the condensation product of C12–C14 alcohol with 5 moles of ethylene oxide) marketed by Hoechst. Preferred range of HLB in these products is from 8–11 and most preferred from 8–10.

Also useful as the non-ionic surfactant of the surfactant systems of the present invention are alkyl polysaccharides disclosed in U.S. Pat. No. 4,565,647, having a hydrophobic group containing from about 6 to about 30 carbon atoms, preferably from about 10 to about 16 carbon atoms and a polysaccharide, e.g. a polyglycoside, hydrophilic group containing from about 1.3 to about 10, preferably from about 1.3 to about 3, most preferably from about 1.3 to about 2.7 saccharide units. Any reducing saccharide containing 5 or 6 carbon atoms can be used, e.g., glucose, galactose and galactosyl moieties can be substituted for the glucosyl moieties (optionally the hydrophobic group is attached at the 2-, 3-, 4-, etc. positions thus giving a glucose or galactose as opposed to a glucoside or galactoside). The intersaccharide bonds can be, e.g., between the one position of the additional saccharide units and the 2-, 3-, 4-, and/or 6-positions on the preceding saccharide units.

The preferred alkylpolyglycosides have the formula

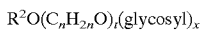

$$R^2O(C_nH_{2n}O)_t(\text{glycosyl})_x$$

wherein $R^2$ is selected from the group consisting of alkyl, alkyl phenyl, hydroxyalkyl, hydroxyalkylphenyl, and mixtures thereof in which the alkyl groups contain from about 10 to about 18, preferably from about 12 to about 14, carbon atoms; n is 2 or 3, preferably 2; t is from 0 to about 10, preferably 0; and x is from about 1.3 to about 10, preferably from about 1.3 to about 3, most preferably from about 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl unit's 2-, 3-, 4-, and/or 6-position, preferably predominantly the 2-position.

The condensation products of ethylene oxide with a hydrophobic base formed by the condensation of propylene oxide with propylene glycol are also suitable for use as the additional non-ionic surfactant systems of the present invention. The hydrophobic portion of these compounds will preferably have a molecular weight from about 1500 to about 1800 and will exhibit water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to about 40 moles of ethylene oxide. Examples of compounds of this type include certain of the commercially available Pluronic™ surfactants, marketed by BASF.

Also suitable for use as the non-ionic surfactant of the non-ionic surfactant system of the present invention, are the condensation products of ethylene oxide with the product resulting from the reaction of propylene oxide and ethylenediamine. The hydrophobic moiety of these products consists of the reaction product of ethylenediamine and excess propylene oxide, and generally has a molecular weight of from about 2500 to about 3000. This hydrophobic moiety is condensed with ethylene oxide to the extent that the condensation product contains from about 40% to about 80% by weight of polyoxyethylene and has a molecular weight of from about 5,000 to about 11,000. Examples of this type of non-ionic surfactant include certain of the commercially available Tetronic™ compounds, marketed by BASF.

Preferred for use as the non-ionic surfactant of the surfactant systems of the present invention are polyethylene oxide condensates of alkyl phenols, condensation products of primary and secondary aliphatic alcohols with from about 1 to about 25 moles of ethyleneoxide, alkylpolysaccharides, and mixtures hereof. Most preferred is $C_8$–$C_{14}$ alkyl phenol ethoxylates having from 3 to 15 ethoxy groups and $C_8$–$C_{18}$ alcohol ethoxylates (preferably $C_{10}$ avg.) having from 2 to 10 ethoxy groups, and mixtures thereof.

Highly preferred non-ionic surfactants are polyhydroxy fatty acid amide surfactants of the formula

wherein $R^1$ is H, or $R^1$ is $C_{1-4}$ hydrocarbyl, 2-hydroxyethyl, 2-hydroxypropyl or a mixture thereof, $R^2$ is $C_{5-31}$ hydrocarbyl, and Z is a polyhydroxy hydrocarbyl having a linear hydrocarbyl chain with at least 3 hydroxyls directly connected to the chain, or an alkoxylated derivative thereof. Preferably, $R^1$ is methyl, $R^2$ is straight $C_{11-15}$ alkyl or $C_{16-18}$ alkyl or alkenyl chain such as coconut alkyl or mixtures thereof, and Z is derived from a reducing sugar such as glucose, fructose, maltose or lactose, in a reductive amination reaction.

Highly preferred anionic surfactants include alkyl alkoxylated sulfate surfactants. Examples hereof are water soluble salts or acids of the formula $RO(A)_m SO3M$ wherein R is an unsubstituted $C_{10}$-$C_{24}$ alkyl or hydroxyalkyl group having a $C_{10}$–$C_{24}$ alkyl component, preferably a $C_{12}$–$C_{20}$ alkyl or hydroxyalkyl, more preferably $C_{12}$–$C_{18}$ alkyl or hydroxyalkyl, A is an ethoxy or propoxy unit, m is greater than zero, typically between about 0.5 and about 6, more preferably between about 0.5 and about 3, and M is H or a cation which can be, for example, a metal cation (e.g., sodium, potassium, lithium, calcium, magnesium, etc.), ammonium or substituted-ammonium cation. Alkyl ethoxylated sulfates as well as alkyl propoxylated sulfates are contemplated herein. Specific examples of substituted ammonium cations include methyl-, dimethyl-, trimethyl-ammonium cations and quaternary ammonium cations such as tetramethyl-ammonium and dimethyl piperdinium cations and those derived from alkylamines such as ethylamine, diethylamine, triethylamine, mixtures thereof, and the like. Exemplary surfactants are $C_{12}$–$C_{18}$ alkyl polyethoxylate (1.0) sulfate ($C_{12}$–$C_{18}E(1.0)M$), $C_{12}$–$C_{18}$ alkyl polyethoxylate (2.25) sulfate ($C_{12}$–$C_{18}(2.25)M$, and $C_{12}$–$C_{18}$ alkyl polyethoxylate (3.0) sulfate ($C_{12}$–$C_{18}E(3.0)M$), and $C_{12}$–$C_{18}$ alkyl polyethoxylate (4.0) sulfate ($C_{12}$–$C_{18}E(4.0)M$), wherein M is conveniently selected from sodium and potassium.

Suitable anionic surfactants to be used are alkyl ester sulfonate surfactants including linear esters of $C_8$–$C_{20}$ carboxylic acids (i.e., fatty acids), which are, sulfonated with gaseous $SO_3$ according to "The Journal of the American Oil Chemists Society", 52 (1975), pp. 323–329. Suitable starting materials would include natural fatty substances as derived from tallow, palm oil, etc.

The preferred alkyl ester sulfonate surfactant, especially for laundry applications, comprise alkyl ester sulfonate surfactants of the structural formula:

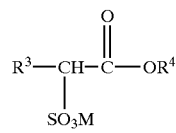

wherein $R^3$ is a $C_8$–$C_{20}$ hydrocarbyl, preferably an alkyl, or combination thereof, $R^4$ is a $C_1$–$C_6$ hydrocarbyl, preferably an alkyl, or combination thereof, and M is a cation, which forms a water-soluble salt with the alkyl ester sulfonate. Suitable salt-forming cations include metals such as sodium, potassium, and lithium, and substituted or unsubstituted ammonium cations, such as monoethanolamine, diethonolamine, and triethanolamine. Preferably, $R^3$ is $C_{10}$–$C_{16}$ alkyl, and $R^4$ is methyl, ethyl or isopropyl. Especially preferred are the methyl ester sulfonates wherein $R^3$ is $C_{10}$–$C_{16}$ alkyl.

Other suitable anionic surfactants include the alkyl sulfate surfactants which are water soluble salts or acids of the formula $ROSO_3M$ wherein R preferably is a $C_{10}$–$C_{24}$ hydrocarbyl, preferably an alkyl or hydroxyalkyl having a $C_{10}$–$C_{20}$ alkyl component, more preferably a $C_{12}$–$C_{18}$ alkyl or hydroxyalkyl, and M is H or a cation, e.g., an alkali metal cation (e.g. sodium, potassium, lithium), or ammonium or substituted ammonium (e.g. methyl-, dimethyl-, and trimethyl ammonium cations and quaternary ammonium cations such as tetramethyl-ammonium and dimethyl piperdinium cations and quaternary ammonium cations derived from alkylamines such as ethylamine, diethylamine, triethylamine, and mixtures thereof, and the like). Typically, alkyl chains of $C_{12}$–$C_{16}$ are preferred for lower wash temperatures (e.g. below about 50° C.) and $C_{16}$–$C_{18}$ alkyl chains are preferred for higher wash temperatures (e.g. above about 50° C.).

Other anionic surfactants useful for detersive purposes can also be included in the laundry detergent compositions of the present invention. Theses can include salts (including, for example, sodium, potassium, ammonium, and substituted ammonium salts such as mono- di- and triethanolamine salts) of soap, $C_8$–$C_{22}$ primary or secondary alkanesulfonates, $C_8$–$C_{24}$ olefinsulfonates, sulfonated polycarboxylic acids prepared by sulfonation of the pyrolyzed product of alkaline earth metal citrates, e.g., as described in British patent specification No. 1,082,179, $C_8$–$C_{24}$ alkylpolyglycolethersulfates (containing up to 10 moles of ethylene oxide); alkyl glycerol sulfonates, fatty acyl glycerol sulfonates, fatty oleyl glycerol sulfates, alkyl phenol ethylene oxide ether sulfates, paraffin sulfonates, alkyl phosphates, isethionates such as the acyl isethionates, N-acyl taurates, alkyl succinamates and sulfosuccinates, monoesters of sulfosuccinates (especially saturated and unsaturated $C_{12}$–$C_{18}$ monoesters) and diesters of sulfosuccinates (especially saturated and unsaturated $C_6$–$C_{12}$ diesters), acyl sarcosinates, sulfates of alkyl polysaccharides such as the sulfates of alkylpolyglucoside (the non-ionic nonsulfated compounds being described below), branched primary alkyl sulfates, and alkyl polyethoxy carboxylates such as those of the formula $RO(CH_2CH_2O)_k$—$CH_2COO$-M+ wherein R is a $C_8$–$C_{22}$ alkyl, k is an integer from 1 to 10, and M is a soluble salt forming cation. Resin acids and hydrogenated resin acids are also suitable, such as rosin, hydrogenated rosin, and resin acids and hydrogenated resin acids present in or derived from tall oil.

Alkylbenzene sulfonates are highly preferred. Especially preferred are linear (straight-chain) alkyl benzene sulfonates (LAS) wherein the alkyl group preferably contains from 10 to 18 carbon atoms.

Further examples are described in "Surface Active Agents and Detergents" (Vol. I and II by Schwartz, Perry and Berch). A variety of such surfactants are also generally disclosed in U.S. Pat. No. 3,929,678, (Column 23, line 58 through Column 29, line 23, herein incorporated by reference).

When included therein, the laundry detergent compositions of the present invention typically comprise from about 1% to about 40%, preferably from about 3% to about 20% by weight of such anionic surfactants.

The laundry detergent compositions of the present invention may also contain cationic, ampholytic, zwitterionic, and semi-polar surfactants, as well as the non-ionic and/or anionic surfactants other than those already described herein.

Cationic detersive surfactants suitable for use in the laundry detergent compositions of the present invention are those having one long-chain hydrocarbyl group. Examples of such cationic surfactants include the ammonium surfactants such as alkyltrimethylammonium halogenides, and those surfactants having the formula:

$$[R^2(OR^3)_y][R^4(OR^3)_y]_2R^5N^+X^-$$

wherein $R^2$ is an alkyl or alkyl benzyl group having from about 8 to about 18 carbon atoms in the alkyl chain, each $R^3$ is selected form the group consisting of —$CH_2CH_2$—, —$CH_2CH(CH_3)$—, —$CH_2CH(CH_2OH)$—, —$CH_2CH_2CH_2$—, and mixtures thereof; each $R^4$ is selected from the group consisting of $C_1$–$C_4$ alkyl, $C_1$–$C_4$ hydroxyalkyl, benzyl ring structures formed by joining the two $R^4$ groups, —$CH_2CHOHCHOHCOR^6CHOHCH_2OH$, wherein $R^6$ is any hexose or hexose polymer having a molecular weight less than about 1000, and hydrogen when y is not 0; $R^5$ is the same as $R^4$ or is an alkyl chain, wherein the total number of carbon atoms or $R^2$ plus $R^5$ is not more than about 18; each y is from 0 to about 10, and the sum of the y values is from 0 to about 15; and X is any compatible anion.

Highly preferred cationic surfactants are the water-soluble quaternary ammonium compounds useful in the present composition having the formula:

$$R_1R_2R_3R_4N^+X^- \qquad (i)$$

wherein $R_1$ is $C_8$–$C_{16}$ alkyl, each of $R_2$, $R_3$ and $R_4$ is independently $C_1$–$C_4$ alkyl, $C_1$–$C_4$ hydroxy alkyl, benzyl, and —$(C_2H_{4O})_xH$ where x has a value from 2 to 5, and X is an anion. Not more than one of $R_2$, $R_3$ or $R_4$ should be benzyl.

The preferred alkyl chain length for $R_1$ is $C_{12}$–$C_{15}$, particularly where the alkyl group is a mixture of chain lengths derived from coconut or palm kernel fat or is derived synthetically by olefin build up or OXO alcohols synthesis.

Preferred groups for $R_2R_3$ and $R_4$ are methyl and hydroxyethyl groups and the anion X may be selected from halide, methosulphate, acetate and phosphate ions.

Examples of suitable quaternary ammonium compounds of formulae (i) for use herein are:
coconut trimethyl ammonium chloride or bromide;
coconut methyl dihydroxyethyl ammonium chloride or bromide;
decyl triethyl ammonium chloride;
decyl dimethyl hydroxyethyl ammonium chloride or bromide;
$C_{12}$–$C_{15}$ dimethyl hydroxyethyl ammonium chloride or bromide;
coconut dimethyl hydroxyethyl ammonium chloride or bromide;
myristyl trimethyl ammonium methyl sulphate;
lauryl dimethyl benzyl ammonium chloride or bromide;
lauryl dimethyl (ethenoxy)$_4$ ammonium chloride or bromide;
choline esters (compounds of formula (i) wherein $R_1$ is

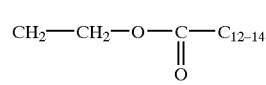

alkyl and $R_2R_3R_4$ are methyl);
di-alkyl imidazolines [compounds of formula (i)].

Other cationic surfactants useful herein are also described in U.S. Pat. No. 4,228,044 and in EP 000 224.

When included therein, the laundry detergent compositions of the present invention typically comprise from 0.2% to about 25%, preferably from about 1% to about 8% by weight of such cationic surfactants.

Ampholytic surfactants are also suitable for use in the laundry detergent compositions of the present invention. These surfactants can be broadly described as aliphatic derivatives of secondary or tertiary amines, or aliphatic derivatives of heterocyclic secondary and tertiary amines in which the aliphatic radical can be straight- or branched-chain. One of the aliphatic substituents contains at least about 8 carbon atoms, typically from about 8 to about 18 carbon atoms, and at least one contains an anionic water-solubilizing group, e.g. carboxy, sulfonate, sulfate. See U.S. Pat. No. 3,929,678 (column 19, lines 18–35) for examples of ampholytic surfactants.

When included therein, the laundry detergent compositions of the present invention typically comprise from 0.2% to about 15%, preferably from about 1% to about 10% by weight of such ampholytic surfactants.

Zwitterionic surfactants are also suitable for use in laundry detergent compositions. These surfactants can be broadly described as derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678 (column 19, line 38 through column 22, line 48) for examples of zwitterionic surfactants.

When included therein, the laundry detergent compositions of the present invention typically comprise from 0.2% to about 15%, preferably from about 1% to about 10% by weight of such zwitterionic surfactants.

Semi-polar nonionic surfactants are a special category of nonionic surfactants which include water-soluble amine oxides containing one alkyl moiety of from about 10 to about 18 carbon atoms and 2 moieties selected from the group consisting of alkyl groups and hydroxyalkyl groups containing from about 1 to about 3 carbon atoms; water-soluble phosphine oxides containing one alkyl moiety of from about 10 to about 18 carbon atoms and 2 moieties selected from the group consisting of alkyl groups and hydroxyalkyl groups containing from about 1 to about 3 carbon atoms; and water-soluble sulfoxides containing one alkyl moiety from about 10 to about 18 carbon atoms and a moiety selected from the group consisting of alkyl and hydroxyalkyl moieties of from about 1 to about 3 carbon atoms.

Semi-polar nonionic detergent surfactants include the amine oxide surfactants having the formula:

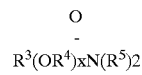

wherein $R^3$ is an alkyl, hydroxyalkyl, or alkyl phenyl group or mixtures thereof containing from about 8 to about 22 carbon atoms; $R^4$ is an alkylene or hydroxyalkylene group containing from about 2 to about 3 carbon atoms or mixtures thereof; x is from 0 to about 3: and each $R^5$ is an alkyl or hydroxyalkyl group containing from about 1 to about 3 carbon atoms or a polyethylene oxide group containing from about 1 to about 3 ethylene oxide groups. The $R^5$ groups can be attached to each other, e.g., through an oxygen or nitrogen atom, to form a ring structure.

These amine oxide surfactants in particular include $C_{10}$–$C_{18}$ alkyl dimethyl amine oxides and $C_8$–$C_{12}$ alkoxy ethyl dihydroxy ethyl amine oxides.

When included therein, the laundry detergent compositions of the present invention typically comprise from 0.2% to about 15%, preferably from about 1% to about 10% by weight of such semi-polar nonionic surfactants.

Builder System

The compositions according to the present invention may further comprise a builder system. Any conventional builder system is suitable for use herein including aluminosilicate materials, silicates, polycarboxylates and fatty acids, materials such as ethylenediamine tetraacetate, metal ion sequestrants such as aminopolyphosphonates, particularly ethylenediamine tetramethylene phosphonic acid and diethylene triamine pentamethylenephosphonic acid. Though less preferred for obvious environmental reasons, phosphate builders can also be used herein.

Suitable builders can be an inorganic ion exchange material, commonly an inorganic hydrated aluminosilicate material, more particularly a hydrated synthetic zeolite such as hydrated zeolite A, X, B, HS or MAP.

Another suitable inorganic builder material is layered silicate, e.g. SKS-6 (Hoechst). SKS-6 is a crystalline layered silicate consisting of sodium silicate ($Na_2Si_2O_5$).

Suitable polycarboxylates containing one carboxy group include lactic acid, glycolic acid and ether derivatives thereof as disclosed in Belgian Patent Nos. 831,368, 821,369 and 821,370. Polycarboxylates containing two carboxy groups include the water-soluble salts of succinic acid, malonic acid, (ethylenedioxy) diacetic acid, maleic acid, diglycollic acid, tartaric acid, tartronic acid and fumaric acid, as well as the ether carboxylates described in German Offenle-enschrift 2,446,686, and 2,446,487, U.S. Pat. No. 3,935,257 and the sulfinyl carboxylates described in Belgian Patent No. 840,623. Polycarboxylates containing three carboxy groups include, in particular, water-soluble citrates, aconitrates and citraconates as well as succinate derivatives such as the carboxymethyloxysuccinates described in British Patent No. 1,379,241, lactoxysuccinates described in Netherlands Application 7205873, and the oxypolycarboxylate materials such as 2-oxa-1,1,3-propane tricarboxylates described in British Patent No. 1,387,447.

Polycarboxylates containing four carboxy groups include oxydisuccinates disclosed in British Patent No. 1,261,829, 1,1,2,2,-ethane tetracarboxylates, 1,1,3,3-propane tetrac7arboxylates containing sulfo substituents include the sulfosuccinate derivatives disclosed in British Patent Nos. 1,398,421 and 1,398,422 and in U.S. Pat. No. 3,936,448, and the sulfonated pyrolysed citrates described in British Patent No. 1,082,179, while polycarboxylates containing phosphone substituents are disclosed in British Patent No. 1,439,000.

Alicyclic and heterocyclic polycarboxylates include cyclopentane-cis,cis-cis-tetracarboxylates, cyclopentadienide pentacarboxylates, 2,3,4,5-tetrahydro-furan-cis, cis, cis-tetracarboxylates, 2,5-tetrahydro-furan-cis, discarboxylates, 2,2,5,5,-tetrahydrofuran-tetracarboxylates, 1,2,3,4,5,6-hexane-hexacarboxylates and carboxymethyl derivatives of polyhydric alcohols such as sorbitol, mannitol and xylitol. Aromatic polycarboxylates include mellitic acid, pyromellitic acid and the phthalic acid derivatives disclosed in British Patent No. 1,425,343.

Of the above, the preferred polycarboxylates are hydroxycarboxylates containing up to three carboxy groups per molecule, more particularly citrates.

Preferred builder systems for use in the present compositions include a mixture of a water-insoluble aluminosilicate builder such as zeolite A or of a layered silicate (SKS-6), and a water-soluble carboxylate chelating agent such as citric acid.

A suitable chelant for inclusion in the detergent compositions in accordance with the invention is ethylenediamine-N,N'-disuccinic acid (EDDS) or the alkali metal, alkaline earth metal, ammonium, or substituted ammonium salts thereof, or mixtures thereof. Preferred EDDS compounds are the free acid form and the sodium or magnesium salt thereof. Examples of such preferred sodium salts of EDDS include $Na_2EDDS$ and $Na_4EDDS$. Examples of such preferred magnesium salts of EDDS include MgEDDS and $Mg_2EDDS$. The magnesium salts are the most preferred for inclusion in compositions in accordance with the invention.

Preferred builder systems include a mixture of a water-insoluble aluminosilicate builder such as zeolite A, and a water soluble carboxylate chelating agent such as citric acid.

Other builder materials that can form part of the builder system for use in granular compositions include inorganic materials such as alkali metal carbonates, bicarbonates, silicates, and organic materials such as the organic phosphonates, amino polyalkylene phosphonates and amino polycarboxylates.

Other suitable water-soluble organic salts are the homo- or co-polymeric acids or their salts, in which the polycarboxylic acid comprises at least two carboxyl radicals separated form each other by not more than two carbon atoms.

Polymers of this type are disclosed in GB-A-1,596,756. Examples of such salts are polyacrylates of MW 2000–5000 and their copolymers with maleic anhydride, such copolymers having a molecular weight of from 20,000 to 70,000, especially about 40,000.

Detergency builder salts are normally included in amounts of from 5% to 80% by weight of the composition. Preferred levels of builder for liquid detergents are from 5% to 30%.

Enzymes

Preferred detergent compositions, in addition to the enzyme preparation of the invention, comprise other enzyme (s) which provides cleaning performance and/or fabric care benefits.

Such enzymes include proteases, lipases, cutinases, amylases, cellulases, peroxidases, oxidases (e.g. laccases).

Proteases: Any protease suitable for use in alkaline solutions can be used. Suitable proteases include those of animal, vegetable or microbial origin. Microbial origin is preferred. Chemically or genetically modified mutants are included. The protease may be a serine protease, preferably an alkaline microbial protease or a trypsin-like protease. Examples of alkaline proteases are subtilisins, especially those derived from Bacillus, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the Fusarium protease described in WO 89/06270.

Preferred commercially available protease enzymes include those sold under the trade names Alcalase, Savinase, Primase, Durazym, and Esperase by Novo Nordisk A/S (Denmark), those sold under the tradename Maxatase, Maxacal, Maxapem, Properase, Purafect and Purafect OXP by Genencor International, and those sold under the tradename Opticlean and Optimase by Solvay Enzymes. Protease enzymes may be incorporated into the compositions in accordance with the invention at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Lipases: Any lipase suitable for use in alkaline solutions can be used. Suitable lipases include those of bacterial or fungal origin. Chemically or genetically modified mutants are included.

Examples of useful lipases include a *Humicola lanuginosa* lipase, e.g., as described in EP 258 068 and EP 305 216, a *Rhizomucor miehei* lipase, e.g., as described in EP 238 023, a Candida lipase, such as a *C. antarctica* lipase, e.g., the *C. antarctica* lipase A or B described in EP 214 761, a Pseudomonas lipase such as a *P. alcaligenes* and *P. pseudoalcaligenes* lipase, e.g., as described in EP 218 272, a *P. cepacia* lipase, e.g., as described in EP 331 376, a *P. stutzeri* lipase, e.g., as disclosed in GB 1,372,034, a *P. fluorescens* lipase, a Bacillus lipase, e.g., a *B. subtilis* lipase (Dartois et al., (1993), Biochemica et Biophysica acta 1131, 253–260), a *B. stearothermophilus* lipase (JP 64/744992) and a *B. pumilus* lipase (WO 91/16422).

Furthermore, a number of cloned lipases may be useful, including the *Penicillium camembertii* lipase described by Yamaguchi et al., (1991), Gene 103, 61–67), the *Geotricum candidum* lipase (Schimada, Y. et al., (1989), J. Biochem., 106, 383–388), and various Rhizopus lipases such as a *R. delemar* lipase (Hass, M. J. et al., (1991), Gene 109, 117–113), a *R. niveus* lipase (Kugimiya et al., (1992), Biosci. Biotech. Biochem. 56, 716–719) and a *R. oryzae* lipase.

Other types of lipolytic enzymes such as cutinases may also be useful, e.g., a cutinase derived from *Pseudomonas mendocina* as described in WO 88/09367, or a cutinase derived from *Fusarium solani pisi* (e.g. described in WO 90/09446).

Especially suitable lipases are lipases such as M1 Lipase™, Luma fast™ and Lipomax™ (Genencor), Lipolase™ and Lipolase Ultra™ (Novo Nordisk A/S), and Lipase P "Amano" (Amano Pharmaceutical Co. Ltd.).

The lipases are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Amylases: Any amylase (a and/or b) suitable for use in alkaline solutions can be used. Suitable amylases include those of bacterial or fungal origin. Chemically or genetically modified mutants are included. Amylases include, for example, a-amylases obtained from a special strain of *B. licheniformis*, described in more detail in GB 1,296,839. Commercially available amylases are Duramyl™, Termamyl™, Fungamyl™ and BAN™ (available from Novo Nordisk A/S) and Rapidase™ and Maxamyl p™ (available from Genencor).

The amylases are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Cellulases: Any cellulase suitable for use in alkaline solutions can be used. Suitable cellulases include those of bacterial or fungal origin. Chemically or genetically modified mutants are included. Suitable cellulases are disclosed in U.S. Pat. No. 4,435,307 which discloses fungal cellulases produced from *Humicola insolens*, in WO 96/34108 and WO 96/34092 which disclose bacterial alkalophilic cellulases (BCE 103) from Bacillus, and in WO 94/21801, U.S. Pat. Nos. 5,475,101 and 5,419,778 which disclose EG III cellulases from Trichoderma. Especially suitable cellulases are the cellulases having colour care benefits. Examples of such cellulases are cellulases described in European patent application No. 0 495 257. Commercially available cellulases include Celluzyme™ and Carezyme™ produced by a strain of Humicola insolens (Novo Nordisk A/S), KAC-500 (B)™ (Kao Corporation), and Puradax™ (Genencor International).

Cellulases are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Peroxidases/Oxidases: Peroxidase enzymes are used in combination with hydrogen peroxide or a source thereof (e.g. a percarbonate, perborate or persulfate). Oxidase enzymes are used in combination with oxygen. Both types of enzymes are used for "solution bleaching", i.e. to prevent transfer of a textile dye from a dyed fabric to another fabric when said fabrics are washed together in a wash liquor, preferably together with an enhancing agent as described in e.g. WO 94/12621 and WO 95/01426. Suitable peroxidases/oxidases include those of plant, bacterial or fungal origin. Chemically or genetically modified mutants are included.

Peroxidase and/or oxidase enzymes are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Mixtures of the above mentioned enzymes are encompassed herein, in particular a mixture of a protease, an amylase, a lipase and/or a cellulase.

The enzyme of the invention, or any other enzyme incorporated in the detergent composition, is normally incorporated in the detergent composition at a level from 0.00001% to 2% of enzyme protein by weight of the composition, preferably at a level from 0.0001% to 1% of enzyme protein by weight of the composition, more preferably at a level from 0.001% to 0.5% of enzyme protein by weight of the composition, even more preferably at a level from 0.01% to 0.2% of enzyme protein by weight of the composition.

Bleaching Agents

Additional optional detergent ingredients that can be included in the detergent compositions of the present invention include bleaching agents such as PB1, PB4 and percarbonate with a particle size of 400–800 microns. These bleaching agent components can include one or more oxygen bleaching agents and, depending upon the bleaching agent chosen, one or more bleach activators. When present oxygen bleaching compounds will typically be present at levels of from about 1% to about 25%. In general, bleaching compounds are optional added components in non-liquid formulations, e.g. granular detergents.

The bleaching agent component for use herein can be any of the bleaching agents useful for detergent compositions including oxygen bleaches as well as others known in the art.

The bleaching agent suitable for the present invention can be an activated or non-activated bleaching agent.

One category of oxygen bleaching agent that can be used encompasses percarboxylic acid bleaching agents and salts thereof. Suitable examples of this class of agents include magnesium monoperoxyphthalate hexahydrate, the magnesium salt of meta-chloro perbenzoic acid, 4-nonylamino-4-oxoperoxybutyric acid and diperoxydodecanedioic acid. Such bleaching agents are disclosed in U.S. Pat. Nos. 4,483,781, 740,446, EP 0 133 354 and U.S. Pat. No. 4,412, 934. Highly preferred bleaching agents also include 6-nonylamino-6-oxoperoxycaproic acid as described in U.S. Pat. No. 4,634,551.

Another category of bleaching agents that can be used encompasses the halogen bleaching agents. Examples of hypohalite bleaching agents, for example, include trichloro isocyanuric acid and the sodium and potassium dichloroisocyanurates and N-chloro and N-bromo alkane sulphonamides. Such materials are normally added at 0.5–10% by weight of the finished product, preferably 1–5% by weight.

The hydrogen peroxide releasing agents can be used in combination with bleach activators such as tetraacetylethylenediamine (TAED), nonanoyloxybenzenesulfonate (NOBS, described in U.S. Pat. No. 4,412,934), 3,5-trimethyl-hexsanoloxybenzenesulfonate (ISONOBS, described in EP 120 591) or pentaacetylglucose (PAG), which are perhydrolyzed to form a peracid as the active bleaching species, leading to improved bleaching effect. In addition, very suitable are the bleach activators C8(6-octanamido-caproyl) oxybenzene-sulfonate, C9(6-nonanamido caproyl) oxybenzenesulfonate and C10 (6-decanamido caproyl) oxybenzenesulfonate or mixtures thereof. Also suitable activators are acylated citrate esters such as disclosed in European Patent Application No. 91870207.7.

Useful bleaching agents, including peroxyacids and bleaching systems comprising bleach activators and peroxygen bleaching compounds for use in cleaning compositions according to the invention are described in application U.S. Pat. No. 08/136,626.

The hydrogen peroxide may also be present by adding an enzymatic system (i.e. an enzyme and a substrate therefore) which is capable of generation of hydrogen peroxide at the beginning or during the washing and/or rinsing process. Such enzymatic systems are disclosed in European Patent Application EP 0 537 381.

Bleaching agents other than oxygen bleaching agents are also known in the art and can be utilized herein. One type of non-oxygen bleaching agent of particular interest includes photoactivated bleaching agents such as the sulfonated zinc and/or aluminium phthalocyanines. These materials can be deposited upon the substrate during the washing process. Upon irradiation with light, in the presence of oxygen, such as by hanging clothes out to dry in the daylight, the sulfonated zinc phthalocyanine is activated and, consequently, the substrate is bleached. Preferred zinc phthalocyanine and a photoactivated bleaching process are described in U.S. Pat. No. 4,033,718. Typically, detergent composition will contain about 0.025% to about 1.25%, by weight, of sulfonated zinc phthalocyanine.

Bleaching agents may also comprise a manganese catalyst. The manganese catalyst may, e.g., be one of the compounds described in "Efficient manganese catalysts for low-temperature bleaching", Nature 369, 1994, pp. 637–639.

Suds Suppressors

Another optional ingredient is a suds suppressor, exemplified by silicones, and silica-silicone mixtures. Silicones can generally be represented by alkylated polysiloxane materials, while silica is normally used in finely divided forms exemplified by silica aerogels and xerogels and hydrophobic silicas of various types. Theses materials can be incorporated as particulates, in which the suds suppressor is advantageously releasably incorporated in a water-soluble or waterdispersible, substantially non surface-active detergent impermeable carrier. Alternatively the suds suppressor can be dissolved or dispersed in a liquid carrier and applied by spraying on to one or more of the other components.

A preferred silicone suds controlling agent is disclosed in U.S. Pat. No. 3,933,672. Other particularly useful suds suppressors are the self-emulsifying silicone suds suppressors, described in German Patent Application DTOS 2,646,126. An example of such a compound is DC-544, commercially available form Dow Corning, which is a siloxane-glycol copolymer. Especially preferred suds controlling agent are the suds suppressor system comprising a mixture of silicone oils and 2-alkyl-alkanols. Suitable 2-alkyl-alkanols are 2-butyl-octanol which are commercially available under the trade name Isofol 12 R.

Such suds suppressor system are described in European Patent Application EP 0 593 841.

Especially preferred silicone suds controlling agents are described in European Patent Application No. 92201649.8. Said compositions can comprise a silicone/silica mixture in combination with fumed nonporous silica such as Aerosil$^R$.

The suds suppressors described above are normally employed at levels of from 0.001% to 2% by weight of the composition, preferably from 0.01% to 1% by weight.

Other Components

Other components used in detergent compositions may be employed such as soil-suspending agents, soil-releasing agents, optical brighteners, abrasives, bactericides, tarnish inhibitors, coloring agents, and/or encapsulated or nonencapsulated perfumes.

Especially suitable encapsulating materials are water soluble capsules which consist of a matrix of polysaccharide and polyhydroxy compounds such as described in GB 1,464,616.

Other suitable water soluble encapsulating materials comprise dextrins derived from ungelatinized starch acid esters of substituted dicarboxylic acids such as described in U.S. Pat. No. 3,455,838. These acid-ester dextrins are, preferably, prepared from such starches as waxy maize, waxy sorghum, sago, tapioca and potato. Suitable examples of said encapsulation materials include N-Lok manufactured by National Starch. The N-Lok encapsulating material consists of a modified maize starch and glucose. The starch is modified by adding monofunctional substituted groups such as octenyl succinic acid anhydride.

Antiredeposition and soil suspension agents suitable herein include cellulose derivatives such as methylcellulose, carboxymethylcellulose and hydroxyethylcellulose, and homo- or co-polymeric polycarboxylic acids or their salts. Polymers of this type include the polyacrylates and maleic anhydride-acrylic acid copolymers previously mentioned as builders, as well as copolymers of maleic anhydride with ethylene, methylvinyl ether or methacrylic acid, the maleic anhydride constituting at least 20 mole percent of the copolymer. These materials are normally used at levels of from 0.5% to 10% by weight, more preferably form 0.75% to 8%, most preferably from 1% to 6% by weight of the composition.

Preferred optical brighteners are anionic in character, examples of which are disodium 4,4'-bis-(2-diethanolamino-4-anilino-s-triazin-6-ylamino)stilbene-2:2' disulphonate, disodium 4,-4'-bis-(2-morpholino-4-anilino-s-triazin-6- ylamino-stilbene-2:2'-disulphonate, disodium 4,4'-bis-(2,4-dianilino-s-triazin-6-ylamino)stilbene-2:2'-disulphonate, monosodium 4', "-bis-(2,4-dianilino-s-tri-azin-6 ylamino) stilbene-2-sulphonate, disodium 4,4'-bis-(2-anilino-4-(N-methyl-N-2-hydroxyethylamino)-s-triazin-6-ylamino) stilbene-2,2'-disulphonate, di-sodium 4,4'-bis-(4-phenyl-2,1,3-triazol-2-yl)-stilbene-2,2' disulphonate, di-so-dium 4,4'bis(2-anilino-4-(1-methyl-2-hydroxyethylamino)-s-triazin-6-ylami-no)stilbene-2,2'disulphonate, sodium 2(stilbyl-4"-(naphtho-1',2':4,5)-1,2,3,-triazole-2"-sulphonate and 4,4'-bis(2-sulphostyryl)biphenyl.

Other useful polymeric materials are the polyethylene glycols, particularly those of molecular weight 1000–10000, more particularly 2000 to 8000 and most preferably about 4000. These are used at levels of from 0.20% to 5% more preferably from 0.25% to 2.5% by weight. These polymers and the previously mentioned homo- or co-polymeric polycarboxylate salts are valuable for improving whiteness maintenance, fabric ash deposition, and cleaning performance on clay, proteinaceous and oxidizable soils in the presence of transition metal impurities.

Soil release agents useful in compositions of the present invention are conventionally copolymers or terpolymers of terephthalic acid with ethylene glycol and/or propylene glycol units in various arrangements. Examples of such polymers are disclosed in U.S. Pat. Nos. 4,116,885 and 4,711,730 and EP 0 272 033. A particular preferred polymer in accordance with EP 0 272 033 has the formula:

$(CH_3(PEG)_{43})_{0.75}(POH)_{0.25}[T\text{-}PO]_{2.8}(T\text{-}PEG)_{0.4}]$
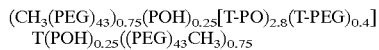
$T(POH)_{0.25}((PEG)_{43}CH_3)_{0.75}$ where PEG is $-(OC_2H_4)O-$, PO is $(OC_3H_6O)$ and T is $(pOOC_6H_4CO)$.

Also very useful are modified polyesters as random copolymers of dimethyl terephthalate, dimethyl sulfoisophthalate, ethylene glycol and 1,2-propanediol, the end groups consisting primarily of sulphobenzoate and secondarily of mono esters of ethylene glycol and/or 1,2-propanediol. The target is to obtain a polymer capped at both end by sulphobenzoate groups, "primarily", in the present context most of said copolymers herein will be endcapped by sulphobenzoate groups. However, some copolymers will be less than fully capped, and therefore their end groups may consist of monoester of ethylene glycol and/or 1,2-propanediol, thereof consist "secondarily" of such species.

The selected polyesters herein contain about 46% by weight of dimethyl terephthalic acid, about 16% by weight of 1,2-propanediol, about 10% by weight ethylene glycol, about 13% by weight of dimethyl sulfobenzoic acid and about 15% by weight of sulfoisophthalic acid, and have a molecular weight of about 3.000. The polyesters and their method of preparation are described in detail in EP 311 342.

Softening Agents

Fabric softening agents can also be incorporated into laundry detergent compositions in accordance with the present invention. These agents may be inorganic or organic in type. Inorganic softening agents are exemplified by the smectite clays disclosed in GB-A-1 400898 and in U.S. Pat. No. 5,019,292. Organic fabric softening agents include the water insoluble tertiary amines as disclosed in GB-A1 514 276 and EP 0 011 340 and their combination with mono $C_{12}$–$C_{14}$ quaternary ammonium salts are disclosed in EP-B-0 026 528 and di-long-chain amides as disclosed in EP 0 242 919. Other useful organic ingredients of fabric softening systems include high molecular weight polyethylene oxide materials as disclosed in EP 0 299 575 and 0 313 146.

Levels of smectite clay are normally in the range from 5% to 15%, more preferably from 8% to 12% by weight, with the material being added as a dry mixed component to the remainder of the formulation. Organic fabric softening agents such as the water-insoluble tertiary amines or dilong chain amide materials are incorporated at levels of from 0.5% to 5% by weight, normally from 1% to 3% by weight whilst the high molecular weight polyethylene oxide materials and the water soluble cationic materials are added at levels of from 0.1% to 2%, normally from 0.15% to 1.5% by weight. These materials are normally added to the spray dried portion of the composition, although in some instances it may be more convenient to add them as a dry mixed particulate, or spray them as molten liquid on to other solid components of the composition.

Polymeric Dye-Transfer Inhibiting Agents

The detergent compositions according to the present invention may also comprise from 0.001% to 10%, preferably from 0.01% to 2%, more preferably form 0.05% to 1% by weight of polymeric dye-transfer inhibiting agents. Said polymeric dye-transfer inhibiting agents are normally incorporated into detergent compositions in order to inhibit the transfer of dyes from colored fabrics onto fabrics washed therewith. These polymers have the ability of complexing or adsorbing the fugitive dyes washed out of dyed fabrics before the dyes have the opportunity to become attached to other articles in the wash.

Especially suitable polymeric dye-transfer inhibiting agents are polyamine N-oxide polymers, copolymers of N-vinyl-pyrrolidone and N-vinylimidazole, polyvinylpyrrolidone polymers, polyvinyloxazolidones and polyvinylimidazoles or mixtures thereof.

Addition of such polymers also enhances the performance of the enzymes according the invention.

The detergent composition according to the invention can be in liquid, paste, gels, bars or granular forms.

Non-dusting granulates may be produced, e.g., as disclosed in U.S. Pat. No. 4,106,991 and 4,661,452 (both to Novo Industri A/S) and may optionally be coated by methods known in the art. Examples of waxy coating materials are poly(ethylene oxide) products (polyethyleneglycol, PEG) with mean molecular weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591.

Granular compositions according to the present invention can also be in "compact form", i.e. they may have a relatively higher density than conventional granular detergents, i.e. form 550 to 950 g/l; in such case, the granular detergent compositions according to the present invention will contain a lower amount of "Inorganic filler salt", compared to conventional granular detergents; typical filler salts are alkaline earth metal salts of sulphates and chlorides, typically sodium sulphate; "Compact" detergent typically comprise not more than 10% filler salt. The liquid compositions according to the present invention can also be in "concentrated form", in such case, the liquid detergent compositions according to the present invention will contain a lower amount of water, compared to conventional liquid detergents. Typically, the water content of the concentrated liquid detergent is less than 30%, more preferably less than 20%, most preferably less than 10% by weight of the detergent compositions.

The compositions of the invention may for example, be formulated as hand and machine laundry detergent compositions including laundry additive compositions and compositions suitable for use in the pretreatment of stained fabrics, rinse added fabric softener compositions, and compositions for use in general household hard surface cleaning operations and dishwashing operations.

The following examples are meant to exemplify compositions for the present invention, but are not necessarily meant to limit or otherwise define the scope of the invention.

In the detergent compositions, the abbreviated component identifications have the following meanings:

LAS: Sodium linear $C_{12}$ alkyl benzene sulphonate
TAS: Sodium tallow alkyl sulphate
XYAS: Sodium $C_{1X}$–$C_{1Y}$ alkyl sulfate
SS: Secondary soap surfactant of formula 2-butyl octanoic acid
25EY: A $C_{12}$–$C_{15}$ predominantly linear primary alcohol condensed with an average of Y moles of ethylene oxide
45EY: A $C_{14}$–$C_{15}$ predominantly linear primary alcohol condensed with an average of Y moles of ethylene oxide
XYEZS: $C_{1X}$–$C_{1Y}$ sodium alkyl sulfate condensed with an average of Z moles of ethylene oxide per mole
Nonionic: $C_{13}$–$C_{15}$ mixed ethoxylated/propoxylated fatty alcohol with an average degree of ethoxylation of 3.8 and an average degree of propoxylation of 4.5 sold under the tradename Plurafax LF404 by BASF Gmbh
CFAA: $C_{12}$–$C_{14}$ alkyl N-methyl glucamide
TFAA: $C_{16}$–$C_{18}$ alkyl N-methyl glucamide
Silicate: Amorphous Sodium Silicate ($SiO_2$:$Na_2O$ ratio=2.0)
NaSKS-6: Crystalline layered silicate of formula d-$Na_2Si_2O_5$
Carbonate: Anhydrous sodium carbonate
Phosphate: Sodium tripolyphosphate
MA/AA: Copolymer of 1:4 maleic/acrylic acid, average molecular weight about 80,000
Polyacrylate: Polyacrylate homopolymer with an average molecular weight of 8,000 sold under the tradename PA30 by BASF GmbH
Zeolite A: Hydrated Sodium Aluminosilicate of formula $Na_{12}(AlO_2SiO_2)_{12}.27H_2O$ having a primary particle size in the range from 1 to 10 micrometers
Citrate: Tri-sodium citrate dihydrate
Citric: Citric Acid
Perborate: Anhydrous sodium perborate monohydrate bleach, empirical formula $NaBO_2.H_2O_2$
PB4: Anhydrous sodium perborate tetrahydrate
Percarbonate: Anhydrous sodium percarbonate bleach of empirical formula $2Na_2CO_3.3H_2O_2$
TAED: Tetraacetyl ethylene diamine
CMC: Sodium carboxymethyl cellulose
DETPMP: Diethylene triamine penta (methylene phosphonic acid), marketed by Monsanto under the Tradename Dequest 2060
PVP: Polyvinylpyrrolidone polymer
EDDS: Ethylenediamine-N, N'-disuccinic acid, [S,S] isomer in the form of the sodium salt
Suds Suppressor: 25% paraffin wax Mpt 50° C., 17% hydrophobic silica, 58% paraffin oil
Granular Suds suppressor: 12% Silicone/silica, 18% stearyl alcohol, 70% starch in granular form
Sulphate: Anhydrous sodium sulphate
HMWPEO: High molecular weight polyethylene oxide
TAE 25: Tallow alcohol ethoxylate (25)

Detergent Example I

A granular fabric cleaning composition in accordance with the invention may be prepared as follows:

| | |
|---|---|
| Sodium linear $C_{12}$ alkyl benzene sulfonate | 6.5 |
| Sodium sulfate | 15.0 |
| Zeolite A | 26.0 |
| Sodium nitrilotriacetate | 5.0 |
| Enzyme of the invention | 0.1 |
| PVP | 0.5 |
| TAED | 3.0 |
| Boric acid | 4.0 |
| Perborate | 18.0 |
| Phenol sulphonate | 0.1 |
| Minors | Up to 100 |

Detergent Example II

A compact granular fabric cleaning composition (density 800 g/l) in accord with the invention may be prepared as follows:

| | |
|---|---|
| 45AS | 8.0 |
| 25E3S | 2.0 |
| 25E5 | 3.0 |
| 25E3 | 3.0 |
| TFAA | 2.5 |
| Zeolite A | 17.0 |
| NaSKS-6 | 12.0 |
| Citric acid | 3.0 |
| Carbonate | 7.0 |
| MA/AA | 5.0 |
| CMC | 0.4 |
| Enzyme of the invention | 0.1 |
| TAED | 6.0 |
| Percarbonate | 22.0 |
| EDDS | 0.3 |
| Granular suds suppressor | 3.5 |
| water/minors | Up to 100% |

Detergent Example III

Granular fabric cleaning compositions in accordance with the invention which are especially useful in the laundering of coloured fabrics were prepared as follows:

| | | |
|---|---|---|
| LAS | 10.7 | — |
| TAS | 2.4 | — |
| TFAA | — | 4.0 |
| 45AS | 3.1 | 10.0 |
| 45E7 | 4.0 | — |
| 25E3S | — | 3.0 |
| 68E11 | 1.8 | — |
| 25E5 | — | 8.0 |
| Citrate | 15.0 | 7.0 |
| Carbonate | — | 10 |
| Citric acid | 2.5 | 3.0 |
| Zeolite A | 32.1 | 25.0 |
| Na-SKS-6 | — | 9.0 |
| MA/AA | 5.0 | 5.0 |
| DETPMP | 0.2 | 0.8 |
| Enzyme of the invention | 0.10 | 0.05 |
| Silicate | 2.5 | — |
| Sulphate | 5.2 | 3.0 |
| PVP | 0.5 | — |
| Poly (4-vinylpyridine) -N-Oxide/copolymer of vinylimidazole and vinylpyrrolidone | — | 0.2 |
| Perborate | 1.0 | — |
| Phenol sulfonate | 0.2 | — |
| Water/Minors | Up to 100% | |

Detergent Example IV

Granular fabric cleaning compositions in accordance with the invention which provide "Softening through the wash" capability may be prepared as follows:

| | | |
|---|---|---|
| 45AS | — | 10.0 |
| LAS | 7.6 | — |
| 68AS | 1.3 | — |
| 45E7 | 4.0 | — |
| 25E3 | — | 5.0 |
| Coco-alkyl-dimethyl hydroxy-ethyl ammonium chloride | 1.4 | 1.0 |
| Citrate | 5.0 | 3.0 |
| Na-SKS-6 | — | 11.0 |
| Zeolite A | 15.0 | 15.0 |
| MA/AA | 4.0 | 4.0 |
| DETPMP | 0.4 | 0.4 |
| Perborate | 15.0 | — |
| Percarbonate | — | 15.0 |
| TAED | 5.0 | 5.0 |
| Smectite clay | 10.0 | 10.0 |
| HMWPEO | — | 0.1 |
| Enzyme of the invention | 0.10 | 0.05 |
| Silicate | 3.0 | 5.0 |
| Carbonate | 10.0 | 10.0 |
| Granular suds suppressor | 1.0 | 4.0 |
| CMC | 0.2 | 0.1 |
| Water/Minors | Up to 100% | |

Detergent Example V

Heavy duty liquid fabric cleaning compositions in accordance with the invention may be prepared as follows:

| | I | II |
|---|---|---|
| LAS acid form | — | 25.0 |
| Citric acid | 5.0 | 2.0 |
| 25AS acid form | 8.0 | — |
| 25AE2S acid form | 3.0 | — |
| 25AE7 | 8.0 | — |
| CFAA | 5 | — |
| DETPMP | 1.0 | 1.0 |
| Fatty acid | 8 | — |
| Oleic acid | — | 1.0 |
| Ethanol | 4.0 | 6.0 |
| Propanediol | 2.0 | 6.0 |
| Enzyme of the invention | 0.10 | 0.05 |
| Coco-alkyl dimethyl hydroxy ethyl ammonium chloride | — | 3.0 |
| Smectite clay | — | 5.0 |
| PVP | 2.0 | — |
| Water/Minors | Up to 100% | |

The Xyloglucan Substrate

In addition to the aforesaid about xyloglucan it should be noted that xyloglucan from tamarind seeds supplied by Megazyme, Ireland has a complex branched structure with glucose, xylose, galactose and arabinose in the ratio of 45:36:16:3. Accordingly, it is strongly believed that an enzyme showing catalytic activity on this xyloglucan also has catalytic activity on other xyloglucan structures from different sources (angiosperms or gymnosperms).

Cotton suspension culture xyloglucan MW 100,000 kDa was obtained from Professor A. Mort of Oklahoma State University. 1H NMR (D2O, 80° C.) of xyloglucans was used to compare the monosaccharide composition of samples of different origin. The integrals of the anomeric signals from the commercial sample fully agree with the composition given by Megazyme. However, the cotton xyloglucan seems to have a different structure. There appears to be much less galactose and about half of galactose residues are fucosy-lated. Furthermore, the molar ratio between xylose and glucose is smaller (0.63 compared to 0.77 for the tamarind), which suggest a more open structure of cotton xyloglucan. These findings agree with results obtained with xyloglucan from cotton cells (Buchala et al, Acta Bot. Neerl. 42, 1993, 213–219).

| Xyloglucan | (Megazyme) | Cotton xyloglucan |
|---|---|---|
| Glucose | 45% | 52% |
| Xylose | 35% | 33% |
| Galactose | 16% | 10% |
| Fucose | — | 5% |
| Arabinose | <4% a | — | a Could not be detected in NMR

Materials and Methods

Strains

*Paenibacillus pabuli*, e.g. the type strain ATCC 43899, and Paenibacillus sp., DSM 13330, comprises a DNA sequence encoding a family 5 xyloglucanase of the invention.

*E. coli*, DSM 13183, comprises the plasmid containing the DNA encoding the xyloglucanase of the invention (SEQ ID NO: 1).

Other strains

*E. coli* hosts: XL1-Blue MRF and XLOLR *E. coli* strains were provided by Stratagene Inc. (USA) and used according to the manufacturer's instructions.

*B. subtilis* PL2306. This strain is the *B. subtilis* DN1885 with disrupted apr and npr genes Diderichsen et al. (1990) disrupted in the transcriptional unit of the known *Bacillus subtilis* cellulase gene, resulting in cellulase negative cells. The disruption was performed essentially as described in Sonenshein et al. (1993).

*Bacillus subtilis* MB1053-1: This strain is PL 2306 in which the pectate lyase gene Pel has been disrupted resulting in a pectate lyase negative strain. The disruption was performed essentially as described in Sonenshein et al. (1993).

Competent cells were prepared and transformed as described by Yasbin et al. (1975).

Plasmids pBK-CAMV: Stratagene inc. La Jolla Calif., USA.

Bacteriophage ZAP Express: Stratagene inc. La Jolla Calif., USA.

pMOL944. This plasmid is a pUB110 derivative essentially containing elements making the plasmid propagatable in *Bacillus subtilis*, kanamycin resistance gene and having a strong promoter and signal peptide cloned from the amyL gene of *B. licheniformis* ATCC 14580. The signal peptide contains a SacII site making it convenient to clone the DNA encoding the mature part of a protein in-fusion with the signal peptide. This results in the expression of a Pre-protein, which is directed towards the exterior of the cell.

The plasmid was constructed by means of ordinary genetic engineering and is briefly described in the following. Construction of pMOL944

The pUB110 plasmid (McKenzie, T. et al., 1986,) was digested with the unique restriction enzyme NciI. A PCR fragment amplified from the amyL promoter encoded on the plasmid pDN1981 (Jørgensen et al., 1990) was digested with NciI and inserted in the NciI digested pUB110 to give the plasmid pSJ2624.

The two PCR primers used have the following sequences:

```
# LWN5494    5'-GTCGCCGGGGCGGCCGCTATCAATTGGTAACTGTATCTCAGC-3'                              (SEQ ID NO:12)

# LWN5495    5'-GTCGCCCGGGAGCTCTGATCAGGTACCAAGCTTGTCGACCTGCAGAATGAGGCAGCAAGAAGAT-3'         (SEQ ID NO:13)
```

The primer #LWN5494 inserts a NotI site in the plasmid.

The plasmid pSJ2624 was then digested with SacI and NotI and a new PCR fragment amplified on amyL promoter encoded on the pDN1981 was digested with SacI and NotI and this DNA fragment was inserted in the SacI-NotI digested pSJ2624 to give the plasmid pSJ2670.

This cloning replaces the first amyL promoter cloning with the same promoter but in the opposite direction. The two primers used for PCR amplification have the following sequences:

minutes centrifugation at 14,000 rpm and the absorbance of the supernatant is measured at 600 nm.

One XyloU unit is defined as the amount of enzyme resulting in an absorbance of 0.24 in a 1 cm cuvette at 600 nm.

Cellulase Assay (CMC Method: CMC Unit)

CMC units is measured using 0.1 M Mops buffer pH 7.5 at 40° C. 20 min incubation and determination of the formation of reducing sugars using PHAB: One CMC unit corresponds to the formation of 1 micromole glucose

```
#LWN5938 5'-GTCGGCGGCCGCTGATCACGTACCAAGCTTGTCGACCTGCAGAATGAGGCAGCAAGAAGAT-3'   (SEQ ID NO:14)

#LWN5939 5'-GTCGGAGCTCTATCAATTGGTAACTGTATCTCAGC-3'                             (SEQ ID NO:15)
```

The plasmid pSJ2670 was digested with the restriction enzymes PstI and BclI and a PCR fragment amplified from a cloned DNA sequence encoding the alkaline amylase SP722 (International Patent Application published as WO95/26397 which is hereby incorporated by reference) was digested with PstI and BclI and inserted to give the plasmid pMOL944. The two primers used for PCR amplification have the following sequence:

equivalent per min. The CMC (Carboxy Methyl Cellulose 7 L from Hercules) final concentration is 0.75%, DS 0.7.

General Molecular Biology Methods

Unless otherwise stated all DNA manipulations and transformations were performed using standard methods of molecular biology (Sambrook et al. (1989) Molecular cloning: A laboratory manual, Cold Spring Harbor lab., Cold Spring Harbor, N.Y.; Ausubel, F. M. et al. (eds.) "Current

```
#LWN7864 5'-AACAGCTGATCACGACTGATCTTTTAGCTTGGCAC-3'        (SEQ ID NO:16)

#LWN7901 5'-AACTGCAGCCGCGGCACATCATAATGGGACAAATGGG-3'     (SEQ ID NO:17)
```

The primer #LWN7901 inserts a SacII site in the plasmid.

Media

TY (as described in Ausubel, F. M. et al. 1995).

LB agar (as described in Ausubel, F. M. et al, 1995).

LBPG is LB agar supplemented with 0.5% Glucose and 0.05 M potassium phosphate, pH 7.0.

AZCL-Xyloglucan is added to LBPG-agar to 0.5% AZCL-Xyloglucan is from Megazyme, Australia.

BPX media is described in EP 0 506 780 (WO 91/09129).

NZY agar (per liter) 5 g of NaCl, 2 g of MgSO4, 5 g of yeast extract, 10 g of NZ amine (casein hydrolysate), 15 g of agar; add deionized water to 1 liter, adjust pH with NaOH to pH 7.5 and autoclave.

NZY broth (per liter) 5 g of NaCl, 2 g of MgSO4, 5 g of yeast extract, 10 g of NZ amine (casein hydrolysate); add deionized water to 1 liter, adjust pH with NaOH to pH 7.5 and autoclave.

NZY Top Agar (per liter) 5 g of NaCl, 2 g of MgSO4, 5 g of yeast extract, 10 g of NZ amine (casein hydrolysate), 0.7% (w/v) agarose; add deionized water to 1 liter, adjust pH with NaOH to pH 7.5 and autoclave.

Xyloglucanase Assay (XyloU)

The xyloglucanase activity is measured using AZCL-xyloglucan from Megazyme, Ireland, as substrate.

A solution of 0.2% of the blue substrate is suspended in a 0.1 M phosphate buffer pH 7.5 under stirring. The solution is distributed under stirring to 1.5 ml Eppendorf tubes (0.75 ml to each), 50 µl enzyme solution is added and they are incubated in an Eppendorp Thermomixer model 5436 for 20 minutes at 40° C. with a mixing of 1200 rpm. After incubation the colored solution is separated from the solid by 4 protocols in Molecular Biology". John Wiley and Sons, 1995; Harwood, C. R., and Cutting, S. M. (eds.) "Molecular Biological Methods for Bacillus". John Wiley and Sons, 1990).

Enzymes for DNA manipulations were used according to the specifications of the suppliers. (e.g. restriction endonucleases, ligases etc. are obtainable from New England Biolabs, Inc.).

The following examples illustrate the invention.

EXAMPLE 1

Cloning of Xyloglucanase Encoding Genes from *Paenibacillus pabuli* and Paenibacillus sp., DSM 13330

Cultivation of Donor Strains

A strain of *Paenibacillus pabuli* was grown in TY with pH adjusted pH 7. After 24 hours incubation at 30° C. and 300 rpm, the cells were harvested and genomic DNA was isolated by the method described below.

Isolation of Genomic DNA

The *Paenibacillus pabuli* strain was propagated in liquid media as described above. The cells were harvested, and genomic DNA was isolated by the method described by Pitcher et al. 1989.

Construction of a Genomic Library from *Paenibacillus pabuli*

Genomic DNA of *Paenibacillus pabuli* was partially digested with restriction enzyme Sau3A, and size-fractionated by electrophoresis on a 0.7% agarose gel (SeaKem agarose, FMC, USA). Fragments between 4 and 10 kb in size were isolated and concentrated to a DNA band by running the DNA fragments backwards on a 1.5% agarose gel followed by extraction of the fragments from the agarose gel slice using the GFX gel extraction kit according to the manufacturer's instructions (Amersham Pharmacia Biotech, USA). To construct a genomic library, ca. 100 ng of purified, fractionated DNA from above was ligated with 1 $\mu$g of BamHI-cleaved, dephosphorylated lambdaZAPexpress vector arms (Stratagene, La Jolla Calif., USA) for 24 hours at +4° C. according to the manufacturer's instructions. A 3-$\mu$l aliquot of the ligation mixture was packaged directly using the GigaPackIII Gold packaging extract (Stratagene, USA) according to the manufacturers instructions (Stratagene). The genomic lambdaZAPExpress phage library was titered using the E. coli XL1-Blue MRF-strain from Stratagene (La Jolla, USA). The unamplified genomic library comprised of 5×10$^6$ plaque-forming units (pfu) with a vector background of less than 1%.

Screening for Xyloglucanase Clones by Functional Expression in lambdaZAPexpress

Approximately 10 000 plaque-forming units (pfu) from the genomic library were plated on NZY-agar plates containing 0.1% AZCL-xyloglucan (MegaZyme, Australia) using E. coli XL1-Blue MRF' (Stratagene, USA) as a host, followed by incubation of the plates at 37° C. for 24 hours. A single xyloglucanase-positive lambda clone was identified by the formation of blue hydrolysis halo around the positive phage clone. The clone was recovered from the screening plate by coring the TOP-agar slice containing the plaque of interest into 500 $\mu$l of SM buffer and 20 $\mu$l of chloroform. The xyloglucanase-positive lambdaZAPExpress clone was plaque-purified by plating an aliquot of the cored phage stock on NZY plates containing 0.1% AZCL-xyloglucan as above. A single, xyloglucanase-positive lambda clone was cored into 500 $\mu$l of SM buffer and 20 $\mu$l of chloroform, and purified by one more plating round as described above.

Single-clone in vivo Excision of the Phagemid from the Xyloglucanase-Positive lambdaZAPExpress Clone E. coli XL1-Blue cells (Stratagene, La Jolla Calif.) were prepared and resuspended in 10 mM MgSO4 as recommended by Stratagene (La Jolla, USA). A 250-$\mu$l aliquot of the pure phage stock from the xyloglucanase-positive clone was combined in Falcon 2059 tube with 200 $\mu$l of XL1-Blue MRF' cells (OD600=1.0) and >10$^6$ pfu/ml of the ExAssist M13 helper phage (Stratagene), and the mixture was incubated at 37° C. for 15 minutes. Three ml of NZY broth was added to the tube and the tube was incubated at 37° C. for 2.5 hours. The tube was heated at 65° C. for 20 minutes to kill the E. coli cells and bacteriophage lambda; the phagemid being resistant to heating. The tube was spun at 3000 rpm for 15 minutes to remove cellular debris and the supernatant was decanted into clean Falcon 2059 tubes. Aliquots of the supernatant containing the excised single-stranded phagemid were used to infect 200 $\mu$l of E. coli XLOLR cells (Stratagene, OD600=1.0 in 10 mM MgSO4) by incubation at 37° C. for 15 minutes. 350 $\mu$l of NZY broth was added to the cells and the tubes were incubated for 45 min at 37° C. Aliquots of the cells were plated onto LB kanamycin agar plates and incubated for 24 hours at 37° C. Five excised single colonies were re-streaked onto LB kanamycin agar plates containing 0.1% AZCL-xyloglucan (MegaZyme, Australia). The xyloglucanase-positive phagemid clones were characterized by the formation of blue hydrolysis halos around the positive colonies. These were further analyzed by restriction enzyme digests of the isolated phagemid DNA (QiaSpin kit, Qiagen, USA) with EcoRI, PstI, EcoRI-PstI, and HindIII followed by agarose gel electrophoresis.

Nucleotide Sequence Analysis 80 ng of target DNA from the genomic xyloglucanase clone pXYG1009 was transposon-tagged using the pGPS-2 donor plasmid and the GPS-1 Genome Priming System from New England Biosystems, USA, according to the manufacturer's instructions. One $\mu$l of the transposition reaction mixture was electroporated into E. coli DH10B cells (Gibco-BRL, USA) according to the manufacturer's instructions, and the transformed E. coli cells were plated on LB agar plates containing kanamycin (20 $\mu$g/ml), and chloramphenicol (15 $\mu$g/ml). 100 colonies were re-tested on LB kanamycin and chloramphenicol plates containing 0.1% AZCL-xyloglucan as substrate, and of these, 13 transposon-tagged pXYG1009 clones, showing no activity on the AZCL-xyloglucan substrate were, together with the pXYG1009 clone, chosen as plasmid templates for sequencing. The nucleotide sequence of the XYG1009 clone was determined from both strands by the dideoxy chain-termination method (Sanger, F., Nicklen, S., and Coulson, A. R. (1977) Proc. Natl. Acad. Sci. U. S. A. 74, 5463–5467) using 500 ng of QiaQuick-purified template (Qiagen, USA), the Taq deoxy-terminal cycle sequencing kit (Perkin-Elmer, USA), fluorescent labelled terminators and 5 pmol of either PBK-CMV polylinker primers (Stratagene, USA) or the primerS and primerN sequencing primers from the GPS-1 Genome Priming System (New England Biosystems, USA). Analysis of the sequence data was performed according to Devereux et al. 1984. The sequence is shown in the appended SEQ ID NO: 1 and the deduced amino acid sequence is shown in the appended SEQ ID NO: 2.

In a similar manner, based on the strain Paenibacillus sp., DSM 13330, the genomic xyloglucanase clone pXYG1022 was identified and analysed. The nucleotide sequence of the XYG1022 enzyme is shown in the appended SEQ ID NO: 3 and the deduced amino acid sequence is shown in the appended SEQ ID NO: 4.

EXAMPLE 2

Identification of Xyloglucanase Genes by PCR Amplification

Total DNA was isolated from different strains of Paenibacillus pabuli or Paenibacillus sp. contemplated to belong to Paenibacillus pabuli using the commercially available kit, High Pure Template Preparation kit (Boehringer Mannheim, catalogue number 1796828) according to the manufacturers instructions.

Primers based on the DNA sequence of XYG1009 (SEQ ID NO: 1) were designed for PCR amplification (polymerase chain reaction) and are given below as Primer 1 and Primer 2. PCR was carried out using the following protocol:

| | |
|---|---|
| Reddy Mix* | 22.5 l |
| Total DNA | 0.5 l |
| Primer 1 (10 M) | 1.0 l |
| Primer 2 (10 M) | 1.0 l |
| | 25.0 l |

*Reddy Mix PCR Master mix (Advanced Biotechnologies Ltd. Surrey KT22 7Ba, UK, catalogue number AB-0575) containing Taq DNA polymerase, dNTPs, MgCl$_2$ and reaction buffer.

The PCR amplification conditions were

| Step 1 | 94° C. | 2 min |
| Step 2 | 94° C. | 30 sec |
| Step 3 | 55° C. | 30 sec |
| Step 4 | 72° C. | 2 min |

Steps 2–4 were repeated for 30 cycles

| Step 5 | 72° C. | 2 min |
| Step 6 | 4° C. | hold temperature |

Five liters of the reaction product was visualised following electrophoresis on a 1% agarose gel. A single band of approx. 1 kb was obtained for each of the samples. The PCR amplified band was sequenced using primers 1 and 2.

Primer 1:
CAT TCT GCA GCC GCG GCA GCG GAC GCT TCG CAA ATA GTG TC (SEQ ID NO:18)

Primer 2:
GCG TTG AGA CGC GCG GCC GCT TAT TGC ATA CCT TGC ATG ATC GC (SEQ ID NO:19)

One of the strains gave a sequence which was 100% identical on the DNA and amino acid sequence listed in SEQ ID NOS: 1 and 2, respectively.

Three other five strains gave the (partial) amino acid sequences listed in SEQ ID NOS: 5–9 as follows:

SEQ ID NO: 5: PCR product denoted XYG 1035 sequenced from N-terminal end

SEQ ID NO: 6: PCR product denoted XYG 1035 sequenced from C-terminal end

SEQ ID NO: 7: PCR product denoted XYG 1036 sequenced and overlapping from both ends SEQ ID NO: 8: PCR product denoted XYG 1037 sequenced from N-terminal end SEQ ID NO: 9: PCR product denoted XYG 1037 sequenced from C-terminal end Comparison of the Amino Acid Sequences from the PCR Amplified DNAs to the Amino Acid Sequence of XYG1009 from *Paenibacillus pabuli* (SEQ ID NO: 2)

The amino acid sequences of the PCR amplified fragments were compared to that of SEQ ID NO: 2 and the number of amino acid substitutions are given below. The nomenclature is such that the numbering is based on the amino acid sequence position in SEQ ID NO: 2. The amino acids are represented by single letters where the letter preceding the number is the amino acid in SEQ ID NO: 2 and the letter following the number is the changed amino acid in the PCR amplified sequence.

In the PCR amplified fragment resulting in XYG 1035 five amino acid substitutions could be detected (N94S, T197A, T241A, F286S, N379K) where the numbering is based on SEQ ID NO: 2.

In the PCR amplified fragment resulting in XYG 1036 8 amino acid substitutions could be detected (R174H, T197A, V224I, Y233F, T241A, Y247F, F286A, S335T) where the numbering is based on SEQ ID NO: 2.

In the PCR amplified fragment resulting in XYG 1037 9 amino acid substitutions could be detected (T197A, A201P, V224I, Y233F, T241V, Y247F, F286A, A290S, A349E) where the numbering is based on SEQ ID NO: 2.

In the PCR amplified fragment resulting in XYG 1034 11 amino acid substitutions could be detected (N61S, E73A, K76Q, V90I, I164V, V224I, Y233F, T241A, Y247F, F286A, S377Q) where the numbering is based on SEQ ID NO: 2.

EXAMPLE 3

Subcloning and Expression in *B. subtilis* of the XYG1009 Gene from *Paenibacillus pabuli* Encoding for the Xyloglucanase of the Invention Subcloning and Expression of Mature Xyloglucanase in *B. subtilis*

The xyloglucanase encoding DNA sequence of the invention (SEQ ID NO: 1) was PCR amplified using the PCR primer set consisting of these two oligo nucleotides:

178765
5'-CAT TCT GCA GCC GCG GCA GCG GAC GCT TCG CAA ATA GTG TC-3' (SEQ ID NO:20)

178766
5'-GCG TTG AGA CGC GCG GCC GCT TAT TGC ATA CCT TGC ATG ATC CC-3' (SEQ ID NO:21)

Restriction sites SacII and NotI are underlined.

The oligonucleotides were used in a PCR reaction in HiFidelity™ PCR buffer (Boehringer Mannheim, Germany) supplemented with 200 µM of each dNTP, 2.6 units of HiFidelity™ Expand enzyme mix and 200 pmol of each primer. Chromosomal DNA isolated from *Paenibacillus pabuli* as described above was used as template.

The PCR reaction was performed using a DNA thermal cycler (Landgraf, Germany). One incubation at 94° C. for 1 min followed by ten cycles of PCR performed using a cycle profile of denaturation at 94° C. for 15 sec, annealing at 60° C. for 60 sec, and extension at 72° C. for 120 sec, followed by twenty cycles of denaturation at 94° C. for 15 sec, 60° C. for 60 sec and 72° C. for 120 sec (at this elongation step 20 sec are added every cycle). Five µl aliquots of the amplification product was analysed by electrophoresis in 0.7% agarose gels (NuSieve, FMC). The appearance of a DNA fragment size 1.2 kb indicated proper amplification of the gene segment.

Subcloning of PCR Fragment

Forty-five µl aliquots of the PCR products generated as described above were purified using QIAquick PCR purification kit (Qiagen, USA) according to the manufacturer's instructions. The purified DNA was eluted in 50 µl of 10 mM Tris-HCl, pH 8.5.

5 µg of pMOL944 and twenty-five-µl of the purified PCR fragment was digested with SacII and NotI, electrophoresed in 0.7% agarose gels (NuSieve, FMC), the relevant fragments were excised from the gels, and purified using QIAquick Gel extraction Kit (Qiagen, USA) according to the manufacturer's instructions. The isolated PCR DNA fragment was then ligated to the SacII-NotI digested and purified pMOL944. The ligation was performed overnight at 16° C. using 0.5 µg of each DNA fragment, 1 U of T4 DNA ligase and T4 ligase buffer (Boehringer Mannheim, Germany).

The ligation mixture was used to transform competent B. subtilis PL2306. The transformed cells were plated onto LBPG-10 µg/ml of Kanamycin-agar plates. After 18 hours incubation at 37° C. colonies were seen on plates. Several clones were analyzed by isolating plasmid DNA from overnight culture broth.

One such positive clone was restreaked several times on agar plates as used above; this clone was called MB1040. The clone MB1040 was grown overnight in TY-10 µg/ml Kanamycin at 37° C., and next day 1 ml of cells were used to isolate plasmid from the cells using the Qiaprep Spin Plasmid Miniprep Kit #27106 according to the manufacturers recommendations for B. subtilis plasmid preparations. This DNA was sequenced and revealed a DNA sequence identical to the part of the xyloglucanase gene in SEQ ID NO: 1 encoding the mature xyloglucanase.

EXAMPLE 4

Expression, Purification and Characterization of Xyloglucanase from *Paenibacillus pabuli*

The clone MB1040 obtained as described above in Example 3 was grown in BPX media with 10 µg/ml of Kanamycin in 500 ml two baffled shake flasks for 5 days at 37° C. at 300 rpm, whereby 4000 ml of culture broth was obtained with a pH of 5.8. Then 180 ml of cationic agent (C521 10%) and 360 ml of anionic agent (A130 0.1%) was added during agitation for flocculation. The flocculated material was separated by centrifugation using a Sorval RC 3B centrifuge at 10000 rpm for 30 min at 6° C. The total volume of the resulting supernatant was 4200 ml.

The supernatant was clarified using Whatman glass filters GF/D and C and finally concentrated on a filtron UF membrane with a cut off of 10 kDa. The total volume of 1450 ml was adjusted to pH 8.0.

For obtaining a highly purified xyloglucanase a final step using Phenyl-Sepharose hydrophobic chromatography was carried out. To the solution was added ammonium sulphate to a final concentration of 1.2 M. The column was adjusted with the same solution and the enzyme solution was added. The xyloglucanase bound to the column and the pure xyloglucanase was eluted using water. The xyloglucanase containing a 95% pure band in SDS-PAGE at 40 kDa was concentrated and formulated with 30% MPG for trials.
Characterisation The pure enzyme gave a single band in SDS-PAGE of 40 kDa and an isoelectric point of around 8.9.

The following sequence was found by N-terminal determination of the pure enzyme: ADASQIVS; the theoretical MW estimated from the found N-terminus ADASQIVS is 40535.06 Da.

The protein concentration was determined using a molar extinction coefficient of 94590 (based on the amino acid composition deducted from the sequence).

The pH activity profiles showed more than 50% relative activity between pH 6.0 and 8.0 at 40° C.

The temperature optimum was 50° at pH 7.5.

The amino acid sequence SEQ ID NO: 2 deducted from the DNA sequence (SEQ ID NO: 1) shows that the coding region code for: positions 1–32 signal peptide, and positions 33–395 catalytic domain belonging to glycosyl hydrolase family 5.

SEQ ID NO: 2 is 83% homologous (Blast) with: CelA EMBL entry: Y12512 (Blanco A., Diaz P., Martinez J., Vidal T., Torres A. L., Pastor F. I. J.; "Cloning of a new endoglucanase gene from Bacillus sp. BP-23 and characterisation of the enzyme. Performance in paper manufacture from cereal straw"; Appl. Microbiol. Biotechnol. 50:48–54(1998)).

SEQ ID NO: 2 is 30% homologous (Blast) with Bacillus agaradhaerens xyloglucanase disclosed in WO 99/02663.

COMPARISON EXAMPLE

Steady State Kinetics on Soluble Xyloglucan and CMC (Carboxymethylcellulose)

A method for determination of activity against xyloglucan has been developed.

The substrate is xyloglucan (amyloid) from tamarind seeds (the substrate is commercially available from Megazyme). Buffer 0.1 M sodium phosphate, pH 7.5.

The substrate was prepared as a stock solution containing 5 gram per 1 in buffer. After mixing it was heated using a magnetic stirrer until a clear solution was obtained. The solution was then cooled to 40° C. and kept in a temperature controlled water bath at 40° C.

The diluted enzyme solution of 0.5 ml was preheated for 10 min. and mixed with 1.0 ml substrate and incubated for 20 min.

The formation of reducing sugars is determined by using p-hydroxy-benzoic-acid-hydrazide (PHBAH) modified from Lever (1972) using 5 gram of potassium sodium tartrate in addition to 1.5 gram of PHBAH. Glucose is used as reference for determination of the reducing groups.
Results On xyloglucan a kCat of 1100 per sec was obtained with a kM of 0.2 gram per 1.

On CMC could only be detected 0.7 kCat per sec with a very high KM above 50 gram per 1.

The xyloglucanase enzyme also had an activity of 0.2 CMC units per mg protein.

In conclusion, the xyloglucanase of the invention is characterised by having a high specific activity on xyloglucan (tamarind gum from Megazyme) and very low cellulase activity on CMC (endoglucanase activity).

Immunological properties: At the Danish company DAKO, rabbit polyclonal monospecific serum was raised against the highly purified xyloglucanase using conventional techniques. The serum formed a nice single precipitate in agarose gels with the xyloglucanase of the invention.

EXAMPLE 5

Subcloning and Expression in *B. subtilis* of the XYG1022 Gene from *Paenibacillus sp.*, DSM 13330, Encoding for the Xyloglucanase of the Invention Subcloning and Expression of Mature Xyloglucanase in *B.subtilis*

The xyloglucanase encoding DNA sequence of the invention was PCR amplified using the PCR primer set consisting of these two oligo nucleotides:

188669:
5'-CATT<u>CTGCAG</u>CCGCGGCCGCGGATTTCAGATCATTGAACGC-3' (SEQ ID NO:22)

189585:
5'-GCGTTGAGACGC<u>GCGGCCGC</u>TTACTGTATACCCTGCATGATGGC-3' (SEQ ID NO:23)

Restriction sites PstI and NotI are underlined

The oligonucleotides were used in a PCR reaction in HiFidelity™ PCR buffer (Boehringer Mannheim, Germany) supplemented with 200 µM of each dNTP, 2.6 units of HiFidelity™ Expand enzyme mix and 200 pmol of each primer. Chromosomal DNA isolated from Paenibacillus sp., DSM 13330, was used as template.

The PCR reaction was performed using a DNA thermal cycler (Landgraf, Germany). One incubation at 94° C. for 1 min followed by ten cycles of PCR performed using a cycle profile of denaturation at 94° C. for 15 sec, annealing at 60° C. for 60 sec, and extension at 72° C for 120 sec, followed by twenty cycles of denaturation at 94° C. for 15 sec, 60° C. for 60 sec and 72° C. for 120 sec (at this elongation step 20 sec are added every cycle). Five µl aliquots of the amplification product was analysed by electrophoresis in 0.7% agarose gels (NuSieve, FMC). The appearance of a DNA fragment size 1.3 kb indicated proper amplification of the gene segment.

Subcloning of PCR Fragment

Forty-five µl aliquots of the PCR products generated as described above were purified using QIAquick PCR purification kit (Qiagen, USA) according to the manufacturer's instructions. The purified DNA was eluted in 50 µl of 10 mM Tris-HCl, pH 8.5.

5 µg of pMOL944 and twenty-five-µl of the purified PCR fragment was digested with PstI and NotI, electrophoresed in 0.7% agarose gels (NuSieve, FMC), the relevant fragments were excised from the gels, and purified using QIAquick Gel extraction Kit (Qiagen, USA) according to the manufacturer's instructions. The isolated PCR DNA fragment was then ligated to the PstI-NotI digested and purified pMOL944. The ligation was performed overnight at 16° C. using 0.5 µg of each DNA fragment, 1 U of T4 DNA ligase and T4 ligase buffer (Boehringer Mannheim, Germany).

The ligation mixture was used to transform competent B. subtilis MB1053-1. The transformed cells were plated onto LBPG-10 µg/ml of Kanamycin-agar plates. After 18 hours incubation at 37° C. colonies were seen on plates. Several clones were analyzed by isolating plasmid DNA from overnight culture broth.

One such positive clone was restreaked several times on agar plates as used above; this clone was called PL3381. The clone PL3381 was grown overnight in TY-10 µg/ml Kanamycin at 37° C., and next day 1 ml of cells were used to isolate plasmid from the cells using the Qiaprep Spin Plasmid Miniprep Kit #27106 according to the manufacturers recommendations for B. subtilis plasmid preparations. This DNA was sequenced and revealed a DNA sequence identical to the part of the xyloglucanase gene in SEQ ID NO: 3 encoding the mature xyloglucanase.

EXAMPLE 6

Purification and Characterization of Xyloglucanase from Paenibacillus sp., DSM 13330

The clone PL3381 obtained as described in example 5 was incubated in 4000 ml of BPX containing 10 µg/ml of Kanamycin and grown for 5 days at 37° C. at 300 rpm, final pH was 5.64.

The fermentation medium was flocculated using cationic flocculation agent C521 (10% solution) and 0.1% solution of anionic agent A130: To 4000 ml of broth was added 180 ml of C521 (10%) simultaneously with 360 ml of A130 under stirring at room temperature. The flocculated material was separated by centrifugation using a Sorval RC 3B centrifuge at 4,500 rpm for 30 minutes. The supernatant was clarified using Whatman glass filter number F. In total was obtained 4000 ml of clear solution.

The liquid was concentrated into 400 ml, using filtron ultrafiltration with a MW cut off of 10 kDa.

The concentrate was batch treated with 200 gram Q-Sepharose equilibrated with 25 mM Tris pH 7.5. The unbound material was stabilized with 30% MPG and the xyloglucanase was used for detergent cleaning. The enzyme is very active in the commercial liquid detergents sold by The Procter & Gamble Company under the brand names Ariel and Tide.

For obtaining a pure enzyme 2 ml of this partial pure enzyme was applied to a size chromatography (Superdex 75) column equilibrated with 0.1 M Sodium acetate pH 6.0. The xyloglucanase eluted as a single peak with a MW of 40 kDa in SDS-PAGE.

After electroblotting of this band the N-terminal was determined as: ADFRSLNASQIVSEMG.

This is in agreement with the amino acid sequence shown in SEQ ID NO: 4 deduced from the DNA sequence shown in SEQ ID NO: 3 with a 32 amino acid pro sequence. The calculated MW from the deduced sequence was 40 kDa and the calculated pI was 8.89. The molar extinction coefficient at 280 nm was 93390.

DSC (Disc Scanning Calorimetry) in sodium acetate buffer at pH 6.0 showed a melting temperature around 68.6° C.

EXAMPLE 7

Subcloning and Expression in B. subtilis of the XYG1034 Gene from Paenibacillus pabuli Encoding for the Xyloglucanase of the Invention Subcloning and Expression of Mature Xyloglucanase in B. subtilis The xyloglucanase encoding DNA sequence of the invention was PCR amplified using the PCR primer set consisting of these two oligo nucleotides:

178765
5'-CAT TCT GCA G<u>CC GCG G</u>CA GCG GAC GCT TCG CAA ATA GTG TC-3' (SEQ ID NO:24)

```
# 178766
5'-GCG TTG AGA CGC GCG GCC GCT TAT TGC ATA CCT TGC ATG ATC GC-3' (SEQ ID
NO:25)
```

Restriction sites SacII and NotI are underlined

The oligonucleotides were used in a PCR reaction in HiFidelity™ PCR buffer (Boehringer Mannheim, Germany) supplemented with 200 µM of each dNTP, 2.6 units of HiFidelity™ Expand enzyme mix and 200 pmol of each primer. Chromosomal DNA isolated from a strain of *Paenibacillus pabuli* was used as template.

The PCR reaction was performed using a DNA thermal cycler (Landgraf, Germany). One incubation at 94° C. for 1 min followed by ten cycles of PCR performed using a cycle profile of denaturation at 94° C. for 15 sec, annealing at 60° C. for 60 sec, and extension at 72° C. for 120 sec, followed by twenty cycles of denaturation at 94° C. for 15 sec, 60° C. for 60 sec and 72° C. for 120 sec (at this elongation step 20 sec are added every cycle). Five µl aliquots of the amplification product was analysed by electrophoresis in 0.7% agarose gels (NuSieve, FMC). The appearance of a DNA fragment size 1.2 kb indicated proper amplification of the gene segment.

Subcloning of PCR Fragment

Forty-five µl aliquots of the PCR products generated as described above were purified using QIAquick PCR purification kit (Qiagen, USA) according to the manufacturer's instructions. The purified DNA was eluted in 50 µl of 10 mM Tris-HCl, pH 8.5.

5 µg of pMOL944 and twenty-five µl of the purified PCR fragment was digested with SacII and NotI, electrophoresed in 0.7% agarose gels (NuSieve, FMC), the relevant fragments were excised from the gels, and purified using QIAquick Gel extraction Kit (Qiagen, USA) according to the manufacturer's instructions. The isolated PCR DNA fragment was then ligated to the SacII-NotI digested and purified pMOL944. The ligation was performed overnight at 16° C. using 0.5 µg of each DNA fragment, 1 U of T4 DNA ligase and T4 ligase buffer (Boehringer Mannheim, Germany).

The ligation mixture was used to transform competent *B. subtilis* PL2306. The transformed cells were plated onto LBPG-10 µg/ml of Kanamycin-agar plates. After 18 hours incubation at 37° C. colonies were seen on plates. Several clones were analyzed by isolating plasmid DNA from overnight culture broth.

One such positive clone was restreaked several times on agar plates as used above, this clone was called MB1067. The clone MB1067 was grown overnight in TY-10 µg/ml Kanamycin at 37° C., and next day 1 ml of cells were used to isolate plasmid from the cells using the Qiaprep Spin Plasmid Miniprep Kit #27106 according to the manufacturers recommendations for *B. subtilis* plasmid preparations. This DNA was sequenced and revealed a DNA sequence identical to the part of the xyloglucanase gene in SEQ ID NO: 10 encoding the mature xyloglucanase represented by the derived protein sequence in SEQ ID NO: 11.

EXAMPLE 8

Purification and Characterization of Xyloglucanase XYG1034 Cloned from *Paenibacillus pabuli*

The clone MB1067 obtained as described in example 7 was incubated in 4200 ml of BPX containing mg/ml kanamycin from shake flasks with a final pH of 7.5.

The fermentation medium was flocculated using 42 ml 50% W/W $CaCl_2$, 42 ml 11% Na-aluminate and 20% formic acid followed by adding 105 ml of C521 (10%) simultaneously with 315 ml of A130 under stirring at room temperature. The flocculated material was separated by centrifugation using a Sorval RC 3B centrifuge at 4,500 rpm for 30 minutes. The supernatant was clarified using Whatman glass filter number F. In total was obtained 3900 ml of clear solution.

The liquid was concentrated into 400 ml, using filtron ultrafiltration with a MW cut off of 10 kDa.

The concentrate was batch treated with 200 gram Q-Sepharose equilibrated with 25 mM Tris pH 7.5. The unbound material was stabilized with 30% MPG and the xyloglucanase was used for detergent cleaning. The enzyme is very active in liquid Ariel and Tide.

For obtaining a pure enzyme 2 ml of this partial pure enzyme was applied to a size chromatography (Superdex 75) column equilibrated with 0.1 M sodium acetate pH 6.0. The xyloglucanase eluted as a single peak with a MW of 40 kDa in SDS-PAGE.

After electroblotting of this band the N-terminal was determined as: ADASQIVSEMGAGWNLG This is in agreement with the amino acid sequence shown in SEQ ID NO: 2 (XYG1009) deduced from the DNA sequence shown in SEQ ID NO: 1 with a 32 amino acid pro sequence. The calculated MW from the deduced sequence was 40 kDa and the calculated pI was 8.89. The molar extinction coefficient at 280 nm was 94590 based on the very homologues sequence of XYG1009.

DSC in sodium acetate buffer at pH 6.0 showed a melting temperature around 61.5° C.

LITERATURE

Ausubel, F. M. et al. (Eds.) "Current protocols in Molecular Biology". John Wiley and Sons, 1995.

N. C. Carpita and D. M. Gibeaut (1993) The Plant Journal 3:1–30.

T. Christensen et al. Biotechnology vol 6 page 1419–1422, 1988.

Devereux et al. (1984) Nucleic Acids Res. 12, 387–395.

Diderichsen, B., Wedsted, U., Hedegaard, L., Jensen, B. R., Sjøholm, C. (1990) Cloning of aldB, which encodes alphaacetolactate decarboxylase, an exoenzyme from Bacillus brevis. J. Bacteriol. 172:4315–4321.

Dretzen, G., Bellard, M., Sassone-Corsi, P., Chambon, P. (1981) A reliable method for the recovery of DNA fragments from agarose and acrylamide gels. Anal. Biochem., 112, 295–298.

Eriksson, O. E. & Hawksworth, D. L.: Systema Ascomycetum vol 12 (1993).

S. C. Fry et al (1992) Biochemical Journal 282:821–828

Hawksworth, D. L., Kirk, P. M., Sutton, B. C. and Pegler, D. N.: Dictionary of the fungi, International Mycological Institute, 616 pp (1995);

T. Hayashi and D. P. Delmer (1988) Carbohydrate Research 181:273–277.

Henrissat, B. 1991. A classification of glycosyl hydrolases based on amino acid sequence similaritites. Biochem. J., 280:309–316.

Henrissat, B., and A. Bairoch. 1993. New families in the classification of glycosyl hydrolases based on amino acid sequence similaritites. Biochem. J., 293:781–788.

Jülich, W.: Higher Taxa of Basidiomycetes, Bibliotheca Mycologia 85, 485 pp (1981).

Jørgensen, P. L. et al., 1990, Gene, 96, p. 37–41.

McKenzie, T. et al., 1986, Plasmid 15:93–103.

Leatherbarrow, R. J. (1992) Grafit version 3.0 Erithacus Software Ltd. Staines, U.K.

Lever, M. (1972) A new reaction for colormetric determination of carbohydrates. Anal. Biochem. 47, 273–279.

O'Donnell, K.:Zygomycetes in culture, University of Georgia, US, 257 pp (1979).

Pitcher, D. G., Saunders, N. A., Owen, R. J. (1989). Rapid extraction of bacterial genomic DNA with guanidium thiocyanate. Lett. Appl. Microbiol., 8, 151–156.

J. K. C. Rose et al (1996) Plant Physiology 110:493–499.

Sanger, F., Nicklen, S., and Coulson, A. R. (1977) Proc. Natl. Acad. Sci. U. S. A. 74, 5463–5467.

A. L. Sonenshein, J. A. Hoch and Richard Losick (Eds.) (1993) *Bacillus subtilis* and other Gram-Positive Bacteria, American Society for microbiology, p.618.

Vincken, J. P., Beldman, G., and Voragen, A. G. J. Substrate-specificity of endoglucanases—what determines xyloglucanase activity. *Carbohydrate Research* 298(4):299–310, 1997.

Von Arx, J. A.: The genera of fungi sporulating in culture, 424 pp (1981).

R. L. Whistler and J. N. BeMiller (1993) Industrial gums: Polysaccharides and their derivatives, Academic Press Inc.

Yasbin, R. E., Wilson, G. A. and Young, F. E. (1975) Transformation and transfection in lysogenic strains of *Bacillus subtilis*: evidence for selective induction of prophage in competent cells. J. Bacteriol, 121:296–304.

W. S. York et al (1996) Carbohydrate Research 285:99–128.

What is claimed is:

1. An isolated xyloglucanase belonging to family 5 of glycosyl hydrolases, which is any of
   (a) a polypeptide having a sequence of at least 90% identity to amino acids 33–395 of SEQ ID NO: 2 when identity is determined by GAP provided in the GCG program package using a GAP creation penalty of 3.0 and GAP extension penalty of 0.1; and
   (b) a polypeptide encoded by a DNA sequence that hybridizes to one or both of the DNA sequence of nucleotides 840–1931 of SEQ ID NO: 1 and nucleotides 693–1896 of SEQ ID NO: 3 under high stringency conditions, wherein the high stringency conditions are hybridization in 5×SSC at 45° C. and washing in 2×SSC at 70° C.

2. The xyloglucanase of claim 1, which is a Paenibacillus xyloglucanase.

3. The xyloglucanase of claim 2, which is a *Paenibacillus pabuli* xyloglucanase.

4. The xyloglucanase of claim 1, which has a sequence that is at least 90% identical to amino acids 33–395 of SEQ ID NO: 2.

5. The xyloglucanase of claim 4, which has a sequence that is at least 95% identical to amino acids 33–395 of SEQ ID NO: 2.

6. The xyloglucanase of claim 5, which has a sequence that is at least 98% identical to amino acids 33–395 of SEQ ID NO: 2.

7. The xyloglucanase of claim 1, which has a sequence which comprises amino acids 33–395 of SEQ ID NO: 2.

8. The xyloglucanase of claim 7, which has a sequence which consists of amino acids 33–395 of SEQ ID NO: 2.

9. The xyloglucanase of claim 1, which is encoded by a DNA sequence that hybridizes to the DNA sequence of nucleotides 840–1931 of SEQ ID NO: 1 under high stringency conditions.

10. The xyloglucanase of claim 1, which is encoded by a DNA sequence that hybridizes to the DNA sequence of nucleotides 693–1896 of SEQ ID NO: 3 under high stringency conditions.

11. An isolated xyloglucanase comprising a sequence of amino acids 33–400 of SEQ ID NO: 4.

12. An isolated xyloglucanase comprising a sequence of amino acids 1–363 of SEQ ID NO: 11.

13. A detergent composition comprising the xyloglucanase of claim 1 and a surfactant.

14. A detergent composition comprising the xyloglucanase of claim 8 and a surfactant.

15. A detergent composition comprising the xyloglucanase of claim 11 and a surfactant.

16. A detergent composition comprising the xyloglucanase of claim 12 and a surfactant.

17. A process for machine treatment of a fabric, which comprises treating the fabric during a washing cycle of a machine washing process with a washing solution which comprises a xyloglucanase of claim 1.

18. A process for machine treatment of a fabric, which comprises treating the fabric during a washing cycle of a machine washing process with a washing solution which comprises a xyloglucanase of claim 8.

19. A process for machine treatment of a fabric, which comprises treating the fabric during a washing cycle of a machine washing process with a washing solution which comprises a xyloglucanase of claim 11.

20. A process for machine treatment of a fabric, which comprises treating the fabric during a washing cycle of a machine washing process with a washing solution which comprises a xyloglucanase of claim 12.

* * * * *

SEQUENCE LISTING

```
<160> NUMBER OF SEQ ID NOS: 25

<210> SEQ ID NO 1
<211> LENGTH: 2392
<212> TYPE: DNA
<213> ORGANISM: Paenibacillus pabuli

<400> SEQUENCE: 1
gatcaaagac ttcattgtat tcaacgagtc agcgcattac cccagtttga agagaaagaa      60
aaattcgtaa agtggttaaa tgggctatta taatatgcat tgagaggagt aagatcatat     120
tgttaagtga attcattgag cttgaagaag agagtgatga gagttaccgg tgttacactc     180
tgcaaaatac agtgcaaata ttcaaacatt gcatacagga tgaggattta aatgacgtcc     240
gaatatatgt gtccacaaat acaccgttag attcaattgt tcataaaata gaagactaca     300
ttaagtggtt ttcaacttgt gagactgtct ttcgagatta ttatgagaat gaacttcagg     360
aaaaagtaca tcaaaattgg ttgaatgaga ttgaagtcta tcgtgtggat atcacattta     420
acagtataac cgactacggc gcaacaatat cttgcggaga tcatattttg cgcgatcaca     480
tcatgattat tgattttgat agagaacaaa ttcaagcaat ccacttaaat ggatagatgg     540
attattttgt agtaaatagt cacaaaaaac aataaagata tcgctttatt ttccataaat     600
gtgttattat gttggtgtcg gacgaagaat tcatttgttt gatcgataga gagaggaggc     660
acgtattctc gaatcattca atctgtatgc atagattaac tgcactgctt gttaaaaata     720
atagaataag cggaggtatg gttatgttca aaaaatggaa gaaatttggc atcagcagct     780
tggcactggt attagtggct gcggtagctt ttaccggatg gagcgctaaa gcatcagcag     840
cggacgcttc gcaaatagtg tctgagatgg gtgcaggatg gaatctcggc aatcagctgg     900
aagcagcggt gaacggtaca ccgaatgaga cagcttgggg caatcctacg gtaactccag     960
agttaatcaa aaaggtaaaa gcggcaggct tcaaatccat tcgtattccc gtttcctatt    1020
tgaacaacat tggaagcgct cccaattata caattaatgc ggcatggctg aatcgaattc    1080
agcaagtcgt ggactatgcg tacaatgaag gtctgtatgt gatcatcaat attcatggtg    1140
atgggtataa ttccgtacag ggtggatggc tgctggtgaa tggtggcaat cagactgcca    1200
ttaaggaaaa atataagaag gtttggcagc agattgccac caagtttagc aactacaatg    1260
```

-continued

```
atcgccttat ttttcgaatcc atgaacgaag tttttgatgg taactatggc aatccaaact  1320
cggcctatta caccaatctg aacgcataca accaaatctt cgtggatacg gttcgtcaga  1380
ctggaggtaa caacaatgcc agatggttgc tagttccagg ctggaacacc aacattgact  1440
acactgttgg taattatggc tttactcttc cgacagataa ttacagatcc tcggctattc  1500
ctagttcgca gaagagaatc atgatctcgg cacactatta ctctccgtgg gattttgcag  1560
gtgaggaaaa cggcaatatc acacagtggg gtgcaacttc tacgaatcct gccaaaaagt  1620
ctacttgggg acaagaggat tatcttgaat cgcaattcaa gtccatgtac acaaatttg  1680
tgactcaggg ctatcctgta gtgattggtg agttcggttc cattgataaa acgtcttacg  1740
attccagcaa caatgtttat cgtgctgcat atgccaaagc agttacagca aaagccaaga  1800
aatacaaaat ggttcctgtg tattgggata acgggcacaa tggtcaacat ggattcgcat  1860
tatttaaccg ttcaaataat accgtgactc agcaaaatat cattaatgcg atcatgcaag  1920
gtatgcaata atttactgtc tatctgcatc cgtgcaaacg gcgtgttcct ccaaaaggga  1980
catgccgttt tttgtgctac ccggagataa agttgaacaa catttaccaa tgcatttac  2040
ataagccaca tacagaattc attaaatccc acactacctt ttatatactt aatttgcttg  2100
atatagcgaa ctaaaaggac taggtggtag acagaatgtt aaaaaagcgt gatttgcagg  2160
aatgccttcc actgtacagt ttaatgatgg accccgcagt ttctccttac gttcgttatg  2220
catgccaatc gtatgaggaa tatctattcc tgacgaaaca attgatggct gaagaagaac  2280
aaaagacagt gatatcccga acgattttga atgaaacagg cagcctatt ggaaccattg  2340
atctatatca tattgagcat caaaccgggt ttttagcccc ttggattgga tc            2392
```

<210> SEQ ID NO 2
<211> LENGTH: 395
<212> TYPE: PRT
<213> ORGANISM: Paenibacillus pabuli

<400> SEQUENCE: 2

```
Met Phe Lys Lys Trp Lys Lys Phe Gly Ile Ser Ser Leu Ala Leu Val
1               5                   10                  15

Leu Val Ala Ala Val Ala Phe Thr Gly Trp Ser Ala Lys Ala Ser Ala
                20                  25                  30

Ala Asp Ala Ser Gln Ile Val Ser Glu Met Gly Ala Gly Trp Asn Leu
            35                  40                  45

Gly Asn Gln Leu Glu Ala Ala Val Asn Gly Thr Pro Asn Glu Thr Ala
        50                  55                  60

Trp Gly Asn Pro Thr Val Thr Pro Glu Leu Ile Lys Lys Val Lys Ala
65                  70                  75                  80

Ala Gly Phe Lys Ser Ile Arg Ile Pro Val Ser Tyr Leu Asn Asn Ile
                85                  90                  95

Gly Ser Ala Pro Asn Tyr Thr Ile Asn Ala Ala Trp Leu Asn Arg Ile
            100                 105                 110

Gln Gln Val Val Asp Tyr Ala Tyr Asn Glu Gly Leu Tyr Val Ile Ile
        115                 120                 125

Asn Ile His Gly Asp Gly Tyr Asn Ser Val Gln Gly Gly Trp Leu Leu
    130                 135                 140

Val Asn Gly Gly Asn Gln Thr Ala Ile Lys Glu Lys Tyr Lys Lys Val
145                 150                 155                 160

Trp Gln Gln Ile Ala Thr Lys Phe Ser Asn Tyr Asn Asp Arg Leu Ile
                165                 170                 175
```

-continued

```
Phe Glu Ser Met Asn Glu Val Phe Asp Gly Asn Tyr Gly Asn Pro Asn
                180                 185                 190

Ser Ala Tyr Tyr Thr Asn Leu Asn Ala Tyr Asn Gln Ile Phe Val Asp
            195                 200                 205

Thr Val Arg Gln Thr Gly Gly Asn Asn Asn Ala Arg Trp Leu Leu Val
        210                 215                 220

Pro Gly Trp Asn Thr Asn Ile Asp Tyr Thr Val Gly Asn Tyr Gly Phe
225                 230                 235                 240

Thr Leu Pro Thr Asp Asn Tyr Arg Ser Ala Ile Pro Ser Ser Gln
                245                 250                 255

Lys Arg Ile Met Ile Ser Ala His Tyr Tyr Ser Pro Trp Asp Phe Ala
                260                 265                 270

Gly Glu Glu Asn Gly Asn Ile Thr Gln Trp Gly Ala Thr Ser Thr Asn
            275                 280                 285

Pro Ala Lys Lys Ser Thr Trp Gly Gln Glu Asp Tyr Leu Glu Ser Gln
        290                 295                 300

Phe Lys Ser Met Tyr Asp Lys Phe Val Thr Gln Gly Tyr Pro Val Val
305                 310                 315                 320

Ile Gly Glu Phe Gly Ser Ile Asp Lys Thr Ser Tyr Asp Ser Ser Asn
                325                 330                 335

Asn Val Tyr Arg Ala Ala Tyr Ala Lys Ala Val Thr Ala Lys Ala Lys
            340                 345                 350

Lys Tyr Lys Met Val Pro Val Tyr Trp Asp Asn Gly His Asn Gly Gln
        355                 360                 365

His Gly Phe Ala Leu Phe Asn Arg Ser Asn Thr Val Thr Gln Gln
370                 375                 380

Asn Ile Ile Asn Ala Ile Met Gln Gly Met Gln
385                 390                 395

<210> SEQ ID NO 3
<211> LENGTH: 2245
<212> TYPE: DNA
<213> ORGANISM: Paenibacillus sp.

<400> SEQUENCE: 3
tggttggcag aagccgataa cgaaattgtc ggcagtattg cagtgatcgg tcattcagat       60
gaaagagctc agattcgatg gtttatcata catccggatt gcagaggcat ggggatcgga      120
aagaagctat tccaggacgc catctcttac tgcagagaaa aagggtaccg cagcgttttt      180
ctggaaacga cggaggatca gaagacggcg atagccatgt ataccaagga aggtttcgtc      240
aaaataaaag aacaagagaa cgatacctgg ggagttcgcc acatcgaaca aacctatgaa      300
cttgagcttt aatgaaaaat agccgctgaa ttaagcggct tttcttgatt gaaggaaaca      360
cgatcgaatt tttatgagtc aggtcatgt atacacatag actggggca gtgtaggga       420 caaactggag gttctccata atcagctctt cagccagagt ttgcttcata tgaagtgagt      480
atatccaaga ttgggacaga ttttcgtcg aaaatccata gagaatattg ttctttaatt       540 tccattttg tgttattatg ttgatgttag gcgattattt catttgtctg atcgatataa       600
aaggagggga catcttctcg attcattcaa ttggtataaa gagagtaacg gcactgcttg      660
taaaaaaatt aaaaataagc ggaggtttgg ttatgctcaa aaaaatgaag aaatatggtg      720
tttgcagttt ggcacttgta ttgtttgcgg ctgcggcatt gaccgggtgg agtactaaag      780
catcggcagc ggatttcaga tcattgaacg cttcacagat tgtatcggag atgggtgcag      840
gatggaatct ggggaatcag cttgaagcaa cagtgaatgg cgtccctagt gaaacggcct      900
```

```
gggcaatcc tgttgttact ccagagttga ttaaaaaggt aaaggcggca ggcttcaaga    960
ccattcgcat tcctgtatcc tatttgaatc atattggaag cgctcccaat tacaccataa  1020
acgcagcgtg gttgaatcga gtccaaaccg tcgttgatta tgcatataat gaaggtttat  1080
atgtcgtcat taacatccat ggagatggct ataattccat cccgggcgga tggcttcttg  1140
tgaatggcag caatcaggct gcaattaagg agaaatacca aaaggtatgg cagcagatag  1200
ctaccaagtt cagcaattat aatgagcgtc ttattttgta atcgatgaac gaagtgttcg  1260
acggaaatta cggcaatccg aatgcggcat actatgctaa cttgaacgct tataatcaaa  1320
tctttgtgga cacggtccgg cagactgggg caacaacaa cgccagatgg ttactgattc   1380
caggctggaa taccaatatt gactatacgg tgggcaatta tggctttgct cttccaacag  1440
atcatttcag atcctcggca attccgagct ctcagaagag aattatgatc tctgcacatt  1500
actactctcc gtgggatttt gctggtgagg agaacgaaa tatcacgcag tggggcgcag   1560
cggcaacaaa tccttcgaag aaatcaacct ggggtcagga agactatctg aatgcacagt  1620
tcaaatcgat gtacgataag tttgtaacac agggctatcc ggttgttatt ggcgaatttg  1680
gctccattga taaaacggcg tatgactcca ccaataacgt atatcgtcaa gcttatgcca  1740
aggcggtaac ggcaactgcc aagaagtacg ggctgtgcc ggtgtattgg acaatggac    1800
ataacggtca gcatggtttc gctttgttta accgctcaaa caacacggtt acccagcaag  1860
gcattattaa tgccatcatg cagggtatac agtaatccag tcatacgttt catcgtatta  1920
aaggcctgtc ctttcataag aaaggacagg ccttttatg cattactcgt ttgttatcac   1980
tcaaacacga atagcatatt gccaaatgaa ttttacataa gccacataca gaattcatta  2040
aactccacaa tacctttat atacttaatt tgcttataca gcgaactaaa aggactaggt   2100
ggtagacaga atgttaaaaa aacgcgattt gcatgaatgc cacgcactgt cagcttattg  2160
aacgacccct cagtgtcacc ttatgttcgt taccaatgtc agtcacctga ggaatatgta  2220
ttcctgacca aacagttgat ggacg                                        2245
```

<210> SEQ ID NO 4
<211> LENGTH: 400
<212> TYPE: PRT
<213> ORGANISM: Paenibacillus sp.

<400> SEQUENCE: 4

```
Met Leu Lys Lys Met Lys Lys Tyr Gly Val Cys Ser Leu Ala Leu Val
1               5                   10                  15

Leu Phe Ala Ala Ala Leu Thr Gly Trp Ser Thr Lys Ala Ser Ala
            20                  25                  30

Ala Asp Phe Arg Ser Leu Asn Ala Ser Gln Ile Val Ser Glu Met Gly
        35                  40                  45

Ala Gly Trp Asn Leu Gly Asn Gln Leu Glu Ala Thr Val Asn Gly Val
    50                  55                  60

Pro Ser Glu Thr Ala Trp Gly Asn Pro Val Thr Pro Glu Leu Ile
65                  70                  75                  80

Lys Lys Val Lys Ala Ala Gly Phe Lys Thr Ile Arg Ile Pro Val Ser
                85                  90                  95

Tyr Leu Asn His Ile Gly Ser Ala Pro Asn Tyr Thr Ile Asn Ala Ala
            100                 105                 110

Trp Leu Asn Arg Val Gln Thr Val Val Asp Tyr Ala Tyr Asn Glu Gly
        115                 120                 125
```

```
Leu Tyr Val Val Ile Asn Ile His Gly Asp Gly Tyr Asn Ser Ile Pro
    130                 135                 140

Gly Gly Trp Leu Leu Val Asn Gly Ser Asn Gln Ala Ala Ile Lys Glu
145                 150                 155                 160

Lys Tyr Gln Lys Val Trp Gln Ile Ala Thr Lys Phe Ser Asn Tyr
                165                 170                 175

Asn Glu Arg Leu Ile Phe Glu Ser Met Asn Glu Val Phe Asp Gly Asn
                180                 185                 190

Tyr Gly Asn Pro Asn Ala Ala Tyr Ala Asn Leu Asn Ala Tyr Asn
            195                 200                 205

Gln Ile Phe Val Asp Thr Val Arg Gln Thr Gly Gly Asn Asn Asn Ala
        210                 215                 220

Arg Trp Leu Leu Ile Pro Gly Trp Asn Thr Asn Ile Asp Tyr Thr Val
225                 230                 235                 240

Gly Asn Tyr Gly Phe Ala Leu Pro Thr Asp His Phe Arg Ser Ser Ala
            245                 250                 255

Ile Pro Ser Ser Gln Lys Arg Ile Met Ile Ser Ala His Tyr Tyr Ser
            260                 265                 270

Pro Trp Asp Phe Ala Gly Glu Glu Asn Gly Asn Ile Thr Gln Trp Gly
            275                 280                 285

Ala Ala Ala Thr Asn Pro Ser Lys Lys Ser Thr Trp Gly Gln Glu Asp
290                 295                 300

Tyr Leu Asn Ala Gln Phe Lys Ser Met Tyr Asp Lys Phe Val Thr Gln
305                 310                 315                 320

Gly Tyr Pro Val Val Ile Gly Glu Phe Gly Ser Ile Asp Lys Thr Ala
                325                 330                 335

Tyr Asp Ser Thr Asn Asn Val Tyr Arg Gln Ala Tyr Ala Lys Ala Val
            340                 345                 350

Thr Ala Thr Ala Lys Lys Tyr Gly Ala Val Pro Val Tyr Trp Asp Asn
            355                 360                 365

Gly His Asn Gly Gln His Gly Phe Ala Leu Phe Asn Arg Ser Asn Asn
    370                 375                 380

Thr Val Thr Gln Gln Gly Ile Ile Asn Ala Ile Met Gln Gly Ile Gln
385                 390                 395                 400

<210> SEQ ID NO 5
<211> LENGTH: 166
<212> TYPE: PRT
<213> ORGANISM: Paenibacillus pabuli

<400> SEQUENCE: 5

Asp Ser Arg Trp Asn Thr Asn Ile Asp Tyr Thr Val Gly Asn Tyr Gly
1               5                   10                  15

Phe Ala Leu Pro Thr Asp Asn Tyr Arg Ser Ser Ala Ile Pro Ser Ser
                20                  25                  30

Gln Lys Arg Ile Met Ile Ser Ala His Tyr Tyr Ser Pro Trp Asp Phe
            35                  40                  45

Ala Gly Glu Glu Asn Gly Asn Ile Thr Gln Trp Gly Ala Thr Ser Thr
    50                  55                  60

Asn Pro Ala Lys Lys Ser Thr Trp Gly Gln Glu Asp Tyr Leu Glu Ser
65                  70                  75                  80

Gln Phe Lys Ser Met Tyr Asp Lys Phe Val Thr Gln Gly Tyr Pro Val
                85                  90                  95

Val Ile Gly Glu Phe Gly Ser Ile Asp Lys Thr Ser Tyr Asp Ser Ser
                100                 105                 110
```

```
Asn Asn Val Tyr Arg Ala Ala Tyr Ala Lys Ala Val Thr Ala Lys Ala
            115                 120                 125

Lys Lys Tyr Lys Met Val Pro Val Tyr Trp Asp Asn Gly His Asn Gly
    130                 135                 140

Gln His Gly Phe Ala Leu Phe Asn Arg Ser Asn Lys Thr Val Thr Gln
145                 150                 155                 160

Gln Asn Ile Ile Asn Trp
                165
```

```
<210> SEQ ID NO 6
<211> LENGTH: 167
<212> TYPE: PRT
<213> ORGANISM: Paenibacillus pabuli

<400> SEQUENCE: 6

Gly Ala Gly Trp Asn Leu Gly Asn Gln Leu Glu Ala Ala Val Asn Gly
1               5                   10                  15

Thr Pro Asn Glu Thr Ala Trp Gly Asn Pro Thr Val Thr Pro Glu Leu
            20                  25                  30

Ile Lys Lys Val Lys Ala Ala Gly Phe Lys Ser Ile Arg Ile Pro Val
        35                  40                  45

Ser Tyr Leu Ser Asn Ile Gly Ser Ala Pro Asn Tyr Thr Ile Asn Ala
    50                  55                  60

Ala Trp Leu Asn Arg Ile Gln Gln Val Val Asp Tyr Ala Tyr Asn Glu
65                  70                  75                  80

Gly Leu Tyr Val Ile Ile Asn Ile His Gly Asp Gly Tyr Asn Ser Val
                85                  90                  95

Gln Gly Gly Trp Leu Leu Val Asn Gly Gly Asn Gln Thr Ala Ile Lys
            100                 105                 110

Glu Lys Tyr Lys Lys Val Trp Gln Gln Ile Ala Thr Lys Phe Ser Asn
        115                 120                 125

Tyr Asn Asp Arg Leu Ile Phe Glu Ser Met Asn Glu Val Phe Asp Gly
    130                 135                 140

Asn Tyr Gly Asn Pro Asn Ser Ala Tyr Tyr Ala Asn Leu Asn Ala Tyr
145                 150                 155                 160

Asn Gln Ile Phe Val Asp Thr
                165
```

```
<210> SEQ ID NO 7
<211> LENGTH: 348
<212> TYPE: PRT
<213> ORGANISM: Paenibacillus pabuli

<400> SEQUENCE: 7

Glu Met Gly Ala Gly Trp Asn Leu Gly Asn Gln Leu Glu Ala Ala Val
1               5                   10                  15

Asn Gly Thr Pro Asn Glu Thr Ala Trp Gly Asn Pro Thr Val Thr Pro
            20                  25                  30

Glu Leu Ile Lys Lys Val Lys Ala Ala Gly Phe Lys Ser Ile Arg Ile
        35                  40                  45

Pro Val Ser Tyr Leu Asn Asn Ile Gly Ser Ala Pro Asn Tyr Thr Ile
    50                  55                  60

Asn Ala Ala Trp Leu Asn Arg Ile Gln Gln Val Val Asp Tyr Ala Tyr
65                  70                  75                  80

Asn Glu Gly Leu Tyr Val Ile Ile Asn Ile His Gly Asp Gly Tyr Asn
                85                  90                  95
```

```
Ser Val Gln Gly Gly Trp Leu Leu Val Asn Gly Asn Gln Thr Ala
            100                 105                 110
Ile Lys Glu Lys Tyr Lys Lys Val Trp Gln Gln Ile Ala Thr Lys Phe
            115                 120                 125
Ser Asn Tyr Asn Asp His Leu Ile Phe Glu Ser Met Asn Glu Val Phe
130                 135                 140
Asp Gly Asn Tyr Gly Asn Pro Asn Ser Ala Tyr Tyr Ala Asn Leu Asn
145                 150                 155                 160
Ala Tyr Asn Gln Ile Phe Val Asp Thr Val Arg Gln Thr Gly Gly Asn
            165                 170                 175
Asn Asn Ala Arg Trp Leu Leu Ile Pro Gly Trp Asn Thr Asn Ile Asp
            180                 185                 190
Phe Thr Val Gly Asn Tyr Gly Phe Ala Leu Pro Thr Asp Asn Phe Arg
            195                 200                 205
Ser Ser Ala Ile Pro Ser Ser Gln Lys Arg Ile Met Ile Ser Ala His
            210                 215                 220
Tyr Tyr Ser Pro Trp Asp Phe Ala Gly Glu Glu Asn Gly Asn Ile Thr
225                 230                 235                 240
Gln Trp Gly Ala Thr Ala Thr Asn Pro Ala Lys Lys Ser Thr Trp Gly
            245                 250                 255
Gln Glu Asp Tyr Leu Glu Ser Gln Phe Lys Ser Met Tyr Asp Lys Phe
            260                 265                 270
Val Thr Gln Gly Tyr Pro Val Val Ile Gly Glu Phe Gly Ser Ile Asp
            275                 280                 285
Lys Thr Ser Tyr Asp Ser Thr Asn Asn Val Tyr Arg Ala Ala Tyr Ala
            290                 295                 300
Lys Ala Val Thr Ala Lys Ala Lys Tyr Lys Met Val Pro Val Tyr
305                 310                 315                 320
Trp Asp Asn Gly His Asn Gly Gln His Gly Phe Ala Leu Phe Asn Arg
            325                 330                 335
Ser Asn Asn Thr Val Thr Gln Gln Asn Ile Ile Asn
            340                 345

<210> SEQ ID NO 8
<211> LENGTH: 160
<212> TYPE: PRT
<213> ORGANISM: Paenibacillus pabuli

<400> SEQUENCE: 8

Gly Ala Gly Trp Asn Leu Gly Asn Gln Leu Glu Ala Ala Val Asn Gly
1               5                   10                  15
Thr Pro Asn Glu Thr Ala Trp Gly Asn Pro Thr Val Thr Pro Glu Leu
            20                  25                  30
Ile Lys Lys Val Lys Ala Ala Gly Phe Lys Ser Ile Arg Ile Pro Val
            35                  40                  45
Ser Tyr Leu Asn Asn Ile Gly Ser Ala Pro Asn Tyr Thr Ile Asn Ala
            50                  55                  60
Ala Trp Leu Asn Arg Ile Gln Gln Val Val Asp Tyr Ala Tyr Asn Glu
65                  70                  75                  80
Gly Leu Tyr Val Ile Ile Asn Ile His Gly Asp Gly Tyr Asn Ser Val
            85                  90                  95
Gln Gly Gly Trp Leu Leu Val Asn Gly Gly Asn Gln Thr Ala Ile Lys
            100                 105                 110
Glu Lys Tyr Lys Lys Val Trp Gln Gln Ile Ala Thr Lys Phe Ser Asn
```

115                 120                 125
Tyr Asn Asp Arg Leu Ile Phe Glu Ser Met Asn Glu Val Phe Asp Gly
            130                 135                 140

Asn Tyr Gly Asn Pro Asn Ser Ala Tyr Tyr Ala Asn Leu Asn Pro Tyr
145                 150                 155                 160

<210> SEQ ID NO 9
<211> LENGTH: 174
<212> TYPE: PRT
<213> ORGANISM: Paenibacillus pabuli

<400> SEQUENCE: 9

Gly Asn Asn Ala Arg Trp Leu Leu Ile Pro Gly Trp Asn Thr Asn
1               5                   10                  15

Ile Asp Phe Thr Val Gly Asn Tyr Gly Phe Val Leu Pro Thr Asp Asn
            20                  25                  30

Phe Arg Ser Ser Ala Ile Pro Ser Gln Lys Arg Ile Met Ile Ser
        35                  40                  45

Ala His Tyr Tyr Ser Pro Trp Asp Phe Ala Gly Glu Glu Asn Gly Asn
    50                  55                  60

Ile Thr Gln Trp Gly Ala Thr Ala Thr Asn Pro Ser Lys Lys Ser Thr
65                  70                  75                  80

Trp Gly Gln Glu Asp Tyr Leu Glu Ser Gln Phe Lys Ser Met Tyr Asp
                85                  90                  95

Lys Phe Val Thr Gln Gly Tyr Pro Val Val Ile Gly Glu Phe Gly Ser
            100                 105                 110

Ile Asp Lys Thr Ser Tyr Asp Ser Ser Asn Val Tyr Arg Ala Ala
        115                 120                 125

Tyr Ala Lys Ala Val Thr Glu Lys Ala Lys Lys Tyr Lys Met Val Pro
    130                 135                 140

Val Tyr Trp Asp Asn Gly His Asn Gly Gln His Gly Phe Ala Leu Phe
145                 150                 155                 160

Asn Arg Ser Asn Asn Thr Val Thr Gln Gln Asn Ile Ile Asn
                165                 170

<210> SEQ ID NO 10
<211> LENGTH: 1092
<212> TYPE: DNA
<213> ORGANISM: Paenibacillus pabuli

<400> SEQUENCE: 10
gcggacgctt cgcaaatagt gtctgagatg ggtgcaggtt ggaatctggg taatcagctg      60
gaagcagcgg taaatggcac accgagtgag acagcttggg gcaatcctac ggtgactccg     120
gcactgattc aaaaagtgaa agctgcgggc ttcaagtcga ttcgtattcc catttcctat     180
ttgaataaca ttggaagcgc tcctaattat acaatcaatg cggcatggct gaatcgaatt     240
cagcaagttg tagattatgc ctacaatgaa ggtctgtatg tcattatcaa tattcatggt     300
gatggttaca attctgtaca gggcggatgg ttgctcgtga atagtggcaa tcagacggcc     360
attaaagaaa gtataaaaa ggtgtggcag caggttgcta ccaagttcag caactataat     420
gatcgtctta tctttgaatc aatgaatgaa gtattcgacg gcaactatgg caacccgaac     480
acggcatatt atgccaatct gaacgcctac aatcaaatct tcgtggatac ggttcgtcag     540
actggaggta caacaatgc cagatggttg ttgattccgg gctggaacac caatattgac     600
ttcacagttg gtaattatgg ttttgcccct tccgacagata atttcagatc ctccgcaatt     660

-continued

```
cctagctcac agaagagaat catgatctcg gcacactatt actccccatg ggattttgca      720
ggtgaagaaa atggcaatat cacgcagtgg ggtgcaacgg caacgaatcc tgccaagaag      780
tctacttggg ggcaagagga ttatctggaa tcgcagttta agtccatgta cgataaattt      840
gtgactcagg gctatcctgt ggtgattggt gaattcggct cgattgataa aacgtcgtac      900
gattccagca acaatgttta tcgtgctgca tacgccaaag cagttacagc aaaagccaag      960
aaatacaaaa tggttcctgt ttattgggac aatgggcata acggtcaaca tgggttcgcc     1020
ttgtttaacc gtcagaataa taccgtgacg caacaaaaca tggttaatgc gatcatgcaa     1080
ggtatgcaat aa                                                         1092
```

<210> SEQ ID NO 11
<211> LENGTH: 363
<212> TYPE: PRT
<213> ORGANISM: Paenibacillus pabuli

<400> SEQUENCE: 11

```
Ala Asp Ala Ser Gln Ile Val Ser Glu Met Gly Ala Gly Trp Asn Leu
 1               5                  10                  15

Gly Asn Gln Leu Glu Ala Ala Val Asn Gly Thr Pro Ser Glu Thr Ala
            20                  25                  30

Trp Gly Asn Pro Thr Val Thr Pro Ala Leu Ile Gln Lys Val Lys Ala
        35                  40                  45

Ala Gly Phe Lys Ser Ile Arg Ile Pro Ile Ser Tyr Leu Asn Asn Ile
    50                  55                  60

Gly Ser Ala Pro Asn Tyr Thr Ile Asn Ala Ala Trp Leu Asn Arg Ile
65                  70                  75                  80

Gln Gln Val Val Asp Tyr Ala Tyr Asn Glu Gly Leu Tyr Val Ile Ile
                85                  90                  95

Asn Ile His Gly Asp Gly Tyr Asn Ser Val Gln Gly Gly Trp Leu Leu
            100                 105                 110

Val Asn Ser Gly Asn Gln Thr Ala Ile Lys Glu Lys Tyr Lys Lys Val
        115                 120                 125

Trp Gln Gln Val Ala Thr Lys Phe Ser Asn Tyr Asn Asp Arg Leu Ile
    130                 135                 140

Phe Glu Ser Met Asn Glu Val Phe Asp Gly Asn Tyr Gly Asn Pro Asn
145                 150                 155                 160

Thr Ala Tyr Tyr Ala Asn Leu Asn Ala Tyr Asn Gln Ile Phe Val Asp
                165                 170                 175

Thr Val Arg Gln Thr Gly Gly Asn Asn Asn Ala Arg Trp Leu Leu Ile
            180                 185                 190

Pro Gly Trp Asn Thr Asn Ile Asp Phe Thr Val Gly Asn Tyr Gly Phe
        195                 200                 205

Ala Leu Pro Thr Asp Asn Phe Arg Ser Ser Ala Ile Pro Ser Ser Gln
    210                 215                 220

Lys Arg Ile Met Ile Ser Ala His Tyr Tyr Ser Pro Trp Asp Phe Ala
225                 230                 235                 240

Gly Glu Glu Asn Gly Asn Ile Thr Gln Trp Gly Ala Thr Ala Thr Asn
                245                 250                 255

Pro Ala Lys Lys Ser Thr Trp Gly Gln Glu Asp Tyr Leu Glu Ser Gln
            260                 265                 270

Phe Lys Ser Met Tyr Asp Lys Phe Val Thr Gln Gly Tyr Pro Val Val
        275                 280                 285

Ile Gly Glu Phe Gly Ser Ile Asp Lys Thr Ser Tyr Asp Ser Ser Asn
```

```
                     290             295             300
Asn Val Tyr Arg Ala Ala Tyr Ala Lys Ala Val Thr Ala Lys Ala Lys
305                 310             315                 320

Lys Tyr Lys Met Val Pro Val Tyr Trp Asp Asn Gly His Asn Gly Gln
                325             330                 335

His Gly Phe Ala Leu Phe Asn Arg Gln Asn Asn Thr Val Thr Gln Gln
            340             345             350

Asn Met Val Asn Ala Ile Met Gln Gly Met Gln
        355             360
```

<210> SEQ ID NO 12
<211> LENGTH: 42
<212> TYPE: DNA
<213> ORGANISM: Artificial Sequence
<220> FEATURE:
<223> OTHER INFORMATION: Primer

<400> SEQUENCE: 12
gtcgccgggg cggccgctat caattggtaa ctgtatctca gc          42

<210> SEQ ID NO 13
<211> LENGTH: 64
<212> TYPE: DNA
<213> ORGANISM: Artificial Sequence
<220> FEATURE:
<223> OTHER INFORMATION: Primer

<400> SEQUENCE: 13
gtcgcccggg agctctgatc aggtaccaag cttgtcgacc tgcagaatga ggcagcaaga    60
agat                                                                64

<210> SEQ ID NO 14
<211> LENGTH: 61
<212> TYPE: DNA
<213> ORGANISM: Artificial Sequence
<220> FEATURE:
<223> OTHER INFORMATION: Primer

<400> SEQUENCE: 14
gtcggcggcc gctgatcacg taccaagctt gtcgacctgc agaatgaggc agcaagaaga    60
t                                                                    61

<210> SEQ ID NO 15
<211> LENGTH: 35
<212> TYPE: DNA
<213> ORGANISM: Artificial Sequence
<220> FEATURE:
<223> OTHER INFORMATION: Primer

<400> SEQUENCE: 15
gtcggagctc tatcaattgg taactgtatc tcagc                  35

<210> SEQ ID NO 16
<211> LENGTH: 35
<212> TYPE: DNA
<213> ORGANISM: Artificial Sequence
<220> FEATURE:
<223> OTHER INFORMATION: Primer

<400> SEQUENCE: 16
aacagctgat cacgactgat cttttagctt ggcac                  35

<210> SEQ ID NO 17
<211> LENGTH: 37
<212> TYPE: DNA
<213> ORGANISM: Artificial Sequence
<220> FEATURE:
<223> OTHER INFORMATION: Primer

<400> SEQUENCE: 17
aactgcagcc gcggcacatc ataatgggac aaatggg                          37

<210> SEQ ID NO 18
<211> LENGTH: 41
<212> TYPE: DNA
<213> ORGANISM: Artificial Sequence
<220> FEATURE:
<223> OTHER INFORMATION: Primer

<400> SEQUENCE: 18
cattctgcag ccgcggcagc ggacgcttcg caaatagtgt c                     41

<210> SEQ ID NO 19
<211> LENGTH: 44
<212> TYPE: DNA
<213> ORGANISM: Artificial Sequence
<220> FEATURE:
<223> OTHER INFORMATION: Primer

<400> SEQUENCE: 19
gcgttgagac gcgcggccgc ttattgcata ccttgcatga tcgc                  44

<210> SEQ ID NO 20
<211> LENGTH: 41
<212> TYPE: DNA
<213> ORGANISM: Artificial Sequence
<220> FEATURE:
<223> OTHER INFORMATION: Primer

<400> SEQUENCE: 20
cattctgcag ccgcggcagc ggacgcttcg caaatagtgt c                     41

<210> SEQ ID NO 21
<211> LENGTH: 44
<212> TYPE: DNA
<213> ORGANISM: Artificial Sequence
<220> FEATURE:
<223> OTHER INFORMATION: Primer

<400> SEQUENCE: 21
gcgttgagac gcgcggccgc ttattgcata ccttgcatga tcgc                  44

<210> SEQ ID NO 22
<211> LENGTH: 41
<212> TYPE: DNA
<213> ORGANISM: Artificial Sequence
<220> FEATURE:
<223> OTHER INFORMATION: Primer

<400> SEQUENCE: 22
cattctgcag ccgcggccgc ggatttcaga tcattgaacg c                     41

<210> SEQ ID NO 23
<211> LENGTH: 44
<212> TYPE: DNA
<213> ORGANISM: Artificial Sequence
<220> FEATURE:
<223> OTHER INFORMATION: Primer -continued

```
<400> SEQUENCE: 23
gcgttgagac gcgcggccgc ttactgtata ccctgcatga tggc        44

<210> SEQ ID NO 24
<211> LENGTH: 41
<212> TYPE: DNA
<213> ORGANISM: Artificial Sequence
<220> FEATURE:
<223> OTHER INFORMATION: Primer

<400> SEQUENCE: 24
cattctgcag ccgcggcagc ggacgcttcg caaatagtgt c           41

<210> SEQ ID NO 25
<211> LENGTH: 44
<212> TYPE: DNA
<213> ORGANISM: Artificial Sequence
<220> FEATURE:
<223> OTHER INFORMATION: Primer

<400> SEQUENCE: 25
gcgttgagac gcgcggccgc ttattgcata ccttgcatga tcgc        44
```